(12) United States Patent
Clark et al.

(10) Patent No.: US 6,951,744 B2
(45) Date of Patent: Oct. 4, 2005

(54) AMPLIFICATION PROCESS

(75) Inventors: Duncan Roy Clark, Farnborough (GB); Suzanne Patricia Vincent, Farnborough (GB)

(73) Assignee: The Secretary of State for Defence, Salisbury (GB)

( * ) Notice: Subject to any disclaimer, the term of this patent is extended or adjusted under 35 U.S.C. 154(b) by 0 days.

(21) Appl. No.: 10/135,807

(22) Filed: Apr. 30, 2002

(65) Prior Publication Data

US 2003/0049655 A1 Mar. 13, 2003

(30) Foreign Application Priority Data

Apr. 30, 2001 (GB) .............................. 0110501

(51) Int. Cl.⁷ .................. C12P 19/34; C07H 21/04; C12N 9/12
(52) U.S. Cl. .................. 435/91.2; 435/194; 536/23.2; 536/23.7
(58) Field of Search .............................. 435/91.2, 194, 435/6, 196, 91.1; 536/23.2, 23.7

(56) References Cited

U.S. PATENT DOCUMENTS

| | | | |
|---|---|---|---|
| 4,808,522 A | * | 2/1989 | Atabekov et al. ............ 435/7.1 |
| 4,868,103 A | | 9/1989 | Stavrianopoulos et al. |
| 5,491,063 A | | 2/1996 | Fisher et al. |
| 5,498,523 A | * | 3/1996 | Tabor et al. .................... 435/6 |
| 5,565,339 A | | 10/1996 | Bloch et al. |
| 5,677,152 A | | 10/1997 | Birch et al. |
| 2001/0055792 A1 | * | 12/2001 | Blakesley .................. 435/91.1 |

FOREIGN PATENT DOCUMENTS

| | | |
|---|---|---|
| EP | A 0810030 | 12/1997 |
| EP | A 0962526 | 12/1999 |
| KR | 10-0292883 | 6/2001 |
| WO | WO 90/12111 A1 | 10/1990 |
| WO | WO 94/05797 A1 | 3/1994 |
| WO | WO 98/22615 A1 | 5/1998 |
| WO | WO 98/24548 | 6/1998 |
| WO | WO 99/28500 | 6/1999 |
| WO | WO 99/28501 | 6/1999 |
| WO | WO 99/42611 | 8/1999 |
| WO | WO 99/66071 | 12/1999 |
| WO | WO 01/62975 A2 | 8/2001 |

OTHER PUBLICATIONS

Kawarabayasi et al in "Complete genome sequence of an aerobic hyper–thermophilic crenarchaeon, Aeropyrum pernix K1" DN Res Apr. 30, 1999;6(2):83–101, 145–52.*
New England Biolabs, Inc., Thermostable Inorganic Pyrophosphatase, Technical Bulletin #M0296, Dec. 14, 2000.
Kawarabayasi et al.; NCBI Protein Sequence Listing: BAA80693.207aa long hypothetical inorganic pyrophosphatase, Jun. 19, 1999.
NCBI Sequence Revision History for BAA80693 updated Mar. 27, 2003.
Heinonen, et al., *Analytical Biochemistry*, 113:313–317 (1981).
Lipman, et al., *Rapid and Sensitive Protein Similarity Searches, Science*, 227:1435–1441 (1985).
Meyer, et al., *Archives of Biochem. And Biophys.*, 319(1):149–156 (1995).
Sako, et al., *Int. J. Syst. Bacteriol.*, 46:1070–1077 (1996).
Stark, et al., *Gene*, 51(2–3):255–267 (1987).
Search Report in priority Application No. GB 0110501.4.

* cited by examiner

*Primary Examiner*—Kenneth R. Horlick
(74) *Attorney, Agent, or Firm*—Kilpatrick Stockton LLP

(57) ABSTRACT

A method for conducting a nucleic acid amplification reaction, said method comprising forming an amplification reaction mixture in the presence of sufficient of a pyrophosphate salt to prevent primer extension taking place, digesting said pyrophosphate salt with a pyrophosphatase enzyme (PPase), and subjecting said reaction mixture to conditions such that an amplification reaction may proceed.

This can be used as a "hot start" amplification.

Particular novel pyrophosphatase enzymes for use in the method are also described and claimed.

25 Claims, 12 Drawing Sheets

Figure 11

Aeropyrum pernix sequence

MWTILPSKTGFVNSLSFITRLAKLSVRRVHAMTGCLKIGPGDEAPDVVNVVIEIPMN
SSVKYEFDKEACIVKVDRFLYTSMVYPFNYGFIPGTLEEDGDPVDVLVISREPVAPG
SLIEAVPVAVLDMEDEEGPDSKVVAVPKAKLDPLFASYKDVGDIPDALKSKIKHFFE
HYKELEPGKWVRVTGWRPAADAKEIIRRAIERYKGA
(SEQ ID NO 2)

```
SEQ ID NO 1
1066801 taatcctaat tcgctttatg tggacgatcc ttcccagcaa aaccgggttt gttaacagcc
1066861 ttagctttat aactcgacta gccaaactat cggttagacg ggtgcatgca atgacaggct
1066921 gtctgaaaat tggtcctgga gatgaggctc cagatgttgt gaatgtcgtt atagagatac
1066981 ctatgaacag ttctgttaag tacgagttcg acaaggaggc gtgtattgtt aaggttgata
1067041 ggttccttta caccagcatg gtctacccct tcaactacgg gttcatacca ggcactctag
1067101 aggaggacgg agatcctgtt gacgttctag ttattagccg ggagcccgtt gctcccggct
1067161 cgcttataga ggctgtgccc gtggccgtgt tagacatgga ggacgaggag ggtccggaca
1067221 gcaaggttgt tgccgtaccc aaggccaagc tggacccct attcgccagc tataaggacg
1067281 ttggcgacat acctgatgcc ctgaaatcca agataaagca cttcttcgag cactataagg
1067341 agctggagcc tggaaagtgg gttagagtga ctggatggag gcctgctgcc gatgcgaagg
1067401 agattataag gagggctata gagaggtata aggggcgtg atgagggctt aacggctcac
1067461 gttttctggg acagtgtcgc acctttgagg gcgatcaccc tcgccagcgt gcgtgtgctt
1067521 ttgtctatga ttatggctac agttcttcta gccgcttcca ccgcccccac agtcaataca
1067581 cttacaccta gagcttctgc gctgtatgct gtggatgtag ttgtagtaga cgccagcaca
1067641 ggatctgccc tggcggttctc ccgtttgtc gtatccgcct acagagggg ggtccgggat
1067701 gtgggtgtta tctactcttc ggcggtctca gtatcagggt ctagtctgga aaggctgctg
```

MTGCLKIGPGDEAPDVVNVVIEIPMNSSVKYEFDKEACIVKVDRFLYTSMVYPFNYG
FIPGTLEEDGDPVDVLVISREPVAPGSLIEAVPVAVLDMEDEEGPDSKVVAVPKAKL
DPLFASYKDVGDIPDALKSKIKHFFEHYKELEPGKWVRVTGWRPAADAKEIIRRAIE
RYKGA    (SEQ ID NO 25)

```
SEQ ID NO 26
atgacaggct gtctgaaaat tggtcctgga gatgaggctc cagatgttgt
gaatgtcgtt atagagatac ctatgaacag ttctgttaag tacgagttcg
acaaggaggc gtgtattgtt aaggttgata ggttccttta caccagcatg
gtctacccct tcaactacgg gttcatacca ggcactctag aggaggacgg
agatcctgtt gacgttctag ttattagccg ggagcccgtt gctcccggct
cgcttataga ggctgtgccc gtggccgtgt tagacatgga ggacgaggag
ggtccggaca gcaaggttgt tgccgtaccc aaggccaagc tggaccccct
attcgccagc tataaggacg ttggcgacat acctgatgcc ctgaaatcca
agataaagca cttcttcgag cactataagg agctggagcc tggaaagtgg
gttagagtga ctggatggag gcctgctgcc gatgcgaagg agattataag
gagggctata gagaggtata aggggcgtg a
```

Figure 12

Alignment of PPase sequences with ClustalW

| | |
|---|---|
| Aeropyrum = *Aeropyrum pernix* | SEQ ID NO 2 |
| Sulfolobus = *Sulfolobus solfataricus* | SEQ ID NO 3 |
| E.coli = *Escherichia coli* | SEQ ID NO 4 |
| Aquifex = *Aquifex aeolicus* | SEQ ID NO 5 |
| Pho = *Pyrococcus horikoshii* | SEQ ID NO 6 |
| Pab = *Pyrococcus abysii* | SEQ ID NO 7 |
| Tli = *Thermococcus litoralis* | SEQ ID NO 8 |
| Themoplasma = *Themoplasma acidophilum* | SEQ ID NO 9 |

```
CLUSTAL W (1.8) multiple sequence alignment aeropyrum     MWTTLPSKTGFVNSLSFITRLAKLSVRRVHAMTGCLKIGP-GDEAPDVVNVVIEIPM-NS
sulfolobus    -----------------------------------MKLSP-GKNAPDVVNVLVEIPQ-GS
E.coli        -------------------------------MSLLNGPA-GKDLPEDIYVVIEIPANAD
aquifex       -------------------------------MGYDQLPP-GKNPPEDIYVVIEIPQ-GS
Pho           --------------------------------MNPFHDLEP-GPNVPEVVYALIEIPK-GS
Pab           --------------------------------MNPFHDLEP-GPNVPEVVYALIEIPK-GS
Tli           --------------------------------MNPFHDLEP-GPEVPEVVYALIEIPK-GS
thermoplasma  --------------------------------MESFYHSVPVGPKPPEEVYVIVEIPR-GS
                                                  .  .  *:  :  . :;***   .

aeropyrum     SVKYEFDKEACIVKVDRFLYTSMVYPFNYGFIPGTLEEDGDPVDVLVISREPVAPGSLIE
sulfolobus    NIKYEYDDEEGVIKVDRVLYTSMNYPFNYGFIPGTLEEDGDPLDVLVITNYQLYPGSVIE
E.coli        PIKYEIDKESGALFVDRFMSTAMFYPCNYGYINHILSLDGDPVDVLVPTPYPLQPGSVIR
aquifex       AVKYELDKDTGVIFVDRLFTAMYYPFNYGFVPQTLADDGDPVDVLVISREPVVPGAVMR
Pho           RNKYELDKETGLLKLDRVLYTPFHYPVDYGIIPRTWYEDGDPFDIMVIMREPTYPLTIIE
Pab           RNKYELDKKTGLLKLDRVLYSPFFYPVDYGIIPRTWYDDDDPFDIMVIMREPTYPLTIIE
Tli           RNKYELDKKTGLIKLDRVLYSPFHYPVDYGIIPQTWYDDDDPFDIMVIMREPTYPGVLIE
thermoplasma  RVKYEIAKDFPGMLVDRVLYSSVVYPVDYGLIPRTLYYDGDPMDVMVLISQPTFPGAIMK
               ***    ..   :  :**.:  :..  **  :**   :        *. **.*::.*       *    ::.

aeropyrum     AVPVAVLDMEDEEGPDSKVVAVPKAKLDPLFASYKDVGDIPDALKSKIKHFFEHYKELEP
sulfolobus    VRPIGILYMKDEEGEDAKIVAVPKDKTDPSFSNIKDINDLPQATKNKIVHFFEHYKELEP
E.coli        CRPVGVLKMTDEAGEDAKLVAVPHSKLSKEYDHIKDVNDLPELLKAQIAHFFEHYKDLEK
aquifex       CRPIGMLEMRDEAGIDTKVIAVPHEKLDPSYSNIKTVDNLPEIVREKIKHFFEHYKELEP
Pho           ARPIGLFKMIDSGDKDYKVLAVPVE--DPYFKDWKDISDVPKAFLDEIAHFFKRYKELE-
Pab           ARPIGLFKMIDSGDKDYKVLAVPVE--DPYFKDWKDIDDVPKAFLDEIAHFFKRYKELQ-
Tli           ARPIGLFKMIDSGDKDYKVLAVPVE--DPYFNDWKDISDVPKAFLDEIAHFFQRYKELQ-
thermoplasma  VRPIGMMKMVDQGETDNKILAVFDK--DPNVSYIKDLKDVNAHLLDEIAKFFSTYKILE-
               *:..:: * *.     *  *:;**      .        *   ::     :*  :**. **  *:

aeropyrum     GKWVRVTGWRPAADAKEIIRRAIERYKGA------
sulfolobus    GKYVKISGWGSATEAKNRIQLAIKRVSGGQZ----
E.coli        GKWVKVEGWENAEAAKAEIVASFER-AKNKZ----
aquifex       GKWVKVENWKGLQDAIEEIKKGIENYKKNKEG---
Pho           GKEIIVEGWEGAEAAKREILRAIEMYKEKFGKKEZ
Pab           GKEIIVEGWECAEAAKREILRAIELYKEKFGSKEZ
Tli           GKEIIVEGWENAEKAKQEILRAIFLYKEKFKKZ--
thermoplasma  KKETKVLGWEGKEAALKEIEVSIKMYEEKYGKKNZ
                *     .*    *    *     .::
```

Figure 13

686bp PCR product. (SEQ ID NO 10)

RE sites in bold, PPase gene in italics, primer sites underlined

```
TGCATGCATATGACAGGCTGTCTGAAAATTGGTCCTGGAGATGAGGCTCCAGATGTTGTGAATGTCGTT
ATAGAGATACCTATGAACAGTTCTGTTAAGTACGAGTTCGACAAGGAGGCGTGTATTGTTAAGGTTGAT
AGGTTCCTTTACACCAGCATGGTCTACCCCTTCAACTACGGGTTCATACCAGGCACTCTAGAGGACGAC
GGAGATCCTGTTGACGTTCTAGTTATTAGCCGGGAGCCCGTTGCTCCCGGCTCGCTTATAGAGGCTGTG
CCCGTGGCCGTGTTAGACATGCAGGACGAGGAGGGTCCGGACAGCAAGGTTGTTGCCGTACCCAAGGCC
AAGCTGGACCCCCTATTCGCCAGCTATAAGGACGTTGGCGACATACCTGATGCCCTGAAATCCAAGATA
AAGCACTTCTTCGAGCACTATAAGGAGCTGGAGCCTGGAAAGTGGGTTAGAGTCACTGGATGGAGGCCT
GCTCCCGATGCGAAGGAGATTATAAGGAGGGCTATAGAGAGGTATAAGGGCGCCGTGATGAGGGCTTAAC
GGCTCACGTTTTCTGGGAGAGTGTCGCACCTTTGAGGGCGATCACCCTCGCCAGCGTGCGTGTGCTTTT
GTCTATGATTATGGCTACAGTTCTTCTAGCCGCTTTCACCGCCCCCACAGTCAAGCTTACACTTA
```

Figure 14

Modified polylinker sequence of pTTQ18NHK from initial ATG to the *Nde* I site and then the *Hin*d III site (SEQ ID NO 11)

```
Met              Nde I
ATGCACCACCACCACCACCATATGGGCATGCTGAATTCGAGCTCGGTACCCGGGGATCCTCTAGAGTCG

ACCTGCAGGCATGCAAGCTT
                Hind III
```

Figure 15 pTTQ18NHK sequence (SEQ ID NO 12)

```
>pTTQ18NHK Sequence
GAACTGCATCTCAACAGCGGTAAGATCCTTGAGAGTTTTCGCCCCGAAGAACGTTTTCCA      60
ATGATGAGCACTTTTAAAGTTCTGCTATGTGGCGCGGTATTATCCCGTATTGACGCCGGG     120
CAAGAGCAACTCGGTCGCCGCATACACTATTCTCAGAATGACTTGGTTGAGTACTCACCA     180
GTCACAGAAAAGCATCTTACGGATGGCATGACAGTAAGAGAATTATGCAGTGCTGCCATA     240
ACCATGAGTGATAACACTGCGGCCAACTTACTTCTGACAACGATCGGAGGACCGAAGGAG     300
CTAACCGCTTTTTTGCACAACATGGGGGATCATGTAACTCGCCTTGATCGTTGGGAACCG     360
GAGCTGAATGAAGCCATACCAAACGACGAGCGTGACACCACGATGCCTGTAGCAATGGCA     420
ACAACGTTGCGCAAACTATTAACTGGCGAACTACTTACTCTAGCTTCCCGGCAACAATTA     480
ATAGACTGGATGGAGGCGGATAAAGTTGCAGGACCACTTCTGCGCTCGGCCCTTCCGGCT     540
GGCTGGTTTATTGCTGATAAATCTGGAGCCGGTGAGCGTGGGTCTCGCGGTATCATTGCA     600
GCACTGGGGCCAGATGCTAAGCCCTCCCGTATCGTAGTTATCTACACGACGGGGAGTCAG     660
GCAACTATGGATGAACGAAATAGACAGATCGCTGAGATAGGTGCCTCACTGATTAAGCAT     720
TGGTAACTGTCAGACCAAGTTTACTCATATATACTTTAGATTGATTTAAAACTTCATTTT     780
TAATTTAAAACGATCTAGGTGAAGATCCTTTTTGATAATCTCATGACCAAAATCCCTTAA     840
CGTGAGTTTTCGTTCCACTGAGCGTCAGACCCCGTAGAAAAGATCAAAGGATCTTCTTGA     900
GATCCTTTTTTTCTGCGCGTAATCTGCTGCTTGCAAACAAAAAAACCACCGCTACCAGCG     960
GTGGTTTGTTTGCCGGATCAAGAGCTACCAACTCTTTTTCCGAAGGTAACTGGCTTCAGC    1020
AGAGCGCAGATACCAAATACTGTCCTTCTAGTGTAGCCGTAGTTAGGCCACCACTTCAAG    1080
AACTCTGTAGCACCGCCTACATACCTCGCTCTGCTAATCCTGTTACCAGTGGCTGCTGCC    1140
AGTGGCGATAAGTCGTGTCTTACCGGGTTGGACTCAAGACGATAGTTACCGGATAAGGCG    1200
CAGCGGTCGGGCTGAACGGGGGGTTCGTGCACACAGCCCAGCTTGGAGCGAACGACCTAC    1260
ACCGAACTGAGATACCTACAGCGTGAGCATTGAGAAAGCGCCACGCTTCCCGAAGGGAGA    1320
AAGGCGGACAGGTATCCGGTAAGCGGCAGGGTCGGAACAGGAGAGCGCACGAGGGAGCTT    1380
CCAGGGGGAAACGCCTGGTATCTTTATAGTCCTGTCGGGTTTCGCCACCTCTGACTTGAG    1440
CGTCGATTTTTGTGATGCTCGTCAGGGGGCGGAGCCTATGAAAAACGCCAGCAACGCG     1500
GCCTTTTTACGGTTCCTGGCCTTTTGCTGGCCTTTTGCTCACATGTTCTTTCCTGCGTTA    1560
TCCCCTGATTCTGTGGATAACCGTATTACCGCCTTTGAGTGACCTGATACCGCTCGCCGC    1620
AGCCGAACGACCGAGCGCAGCGAGTCAGTGAGCGAGGAAGCGGAAGAGCGCCCAATACGC    1680
AAACGCCTCTCCCCGCGCGTTGGCGGATTCATTAATGCAGAATTAATTCTCATGTTTCA    1740
CAGCTTATCATCGACTGCACGGTGCACCAATGCTTCTGGCGTCAGGCAGCCATCGGAAGC    1800
TGTGGTATGGCTGTGCAGGTCGTAAATCACTGCATAATTCGTGTCGCTCAAGGCGCACTC    1860
CCGTTCTGGATAATGTTTTTGCGCCGACATCATAACGGTTCTGGCAAATATTCTGAAAT    1920
GAGCTGTTGACAATTAATCATCGGCTCGTATAATGTGTGGAATTGTGAGCGGATAACAAT    1980
TTCACACAGGAAACACATATATGCACCACCACCACCACCATATGGGCATGCTGAATTCGA    2040
GCTCGGTACCCGGGGATCCTCTAGAGTCGACCTGCAGGCATGCAAGCTTGGCACTGGCCG    2100
TCGTTTTACAACGTCGTGACTGGGAAAACCCTGGCGTTACCCAACTTAATCGCCTTGCAG    2160
CACATCCCCCTTTCGCCAGCTGGCGTAATAGCGAAGAGGCCCGCACCGATCGCCCTTCCC    2220
AACAGTTGCGCAGCCTGAATGGCGAATGGCGCCTGATGCGGTATTTTCTCCTTACGCATC    2280
TGTGCGGTATTTCACACCGCATAAATTCCCTGTTTTGGCGGATGAGAGAAGATTTTCAGC    2340
CTGATACAGATTAAATCAGAACGCAGAAGCGGTCTGATAAAACAGAATTTGCCTGGCGGC    2400
AGTAGCGCGGTGGTCCCACCTGACCCCATGCCGAACTCAGAAGTGAAACGCCGTAGCGCC    2460
GATGGTAGTGTGGGGTCTCCCCATGCGAGAGTAGGGAACTGCCAGGCATCAAATAAAACG    2520
AAAGGCTCAGTCGAAAGACTGGGCCTTTCGTTTTATCTGTTGTTTGTCGGTGAACGCTCT    2580
CCTGAGTAGGACAAATCCGCCGGGAGCGGATTTGAACGTTGCGAAGCAACGGCCCGGAGG    2640
GTGGCGGGCAGGACGCCCGCCATAAACTGCCAGGCATCAAATTAAGCAGAAGGCCATCCT    2700
GACGGATGGCCTTTTTGCGTTTCTACAAACTCTTCCTGTCGTCATATCTACAAGCCATCC    2760
CCCCACAGATACGGTAAACTAGCCTCGTTTTTGCATCAGGAAAGCAGGGAATTTATGCTG    2820
CACTCTCAGTACAATCTGCTCTGATGCCGCATAGTTAAGCCAGCCCCGACACCCGCCAAC    2880
ACCCGCTGACGCGCCCTGACGGGCTTGTCTGCTCCCGGCATCCGCTTACAGACAAGCTGT    2940
GACCGTCTCCGGGAGCTGCATGTGTCAGAGGTTTTCACCGTCATCACCGAAACGCGCGAG    3000
ACGAAAGGGCCTGATTAGAAAACTCATCGAGCATCAAATGAAACTGCAATTTATTCATA    3060
TCAGGATTATCAATACCATATTTTGAAAAAGCCGTTTCTGTAATGAAGGAGAAAACTCA    3120
CCGAGGCAGTTCCATAGGATGGCAAGATCCTGGTATCGGTCTGCGATTCCGACTCGTCCA    3180
ACATCAATACAACCTATTAATTTCCCCTCGTCAAAAATAAGGTTATCAAGTGAGAAATCA    3240
CCATGAGTGACGACTGAATCCGGTGAGAATGGCAAAAGNTTATGCATTTCTTTCCAGACT    3300
TGTTCAACAGGCCAGCCATTACGCTCGTCATCAAAATCACTCGCATCAACCAAACCGTTA    3360
TTCATTCGTGATTGCGCCTGAGCGAGACGAAATACGCGATCGCTGTTAAAAGGACAATTA    3420
CAAACAGGAATCGAATGCAACCGGCGCAGGAACACTGCCAGCGCATCAACAATATTTTCA    3480
CCTGAATCAGGATATTCTTCTAATACCTGGAATGCTGTTTTCCCNGGGATCGCAGTGGTG    3540
AGTAACCATGCATCATCAGGAGTACGGATAAAATGCTTGATGGTCGGAAGAGGCATAAAT    3600
TCCGTCAGCCAGTTTAGTCTGACCATCTCATCTGTAACATCATTGGCAACGCTACCTTTG    3660
CCATGTTTCAGAAACAACTCTGGCGCATCGGGCTTCCCATACAATCGATAGATTGTCGCA    3720
CCTGATTGCCCGACATTATCGCGAGCCCATTTATACCCATATAAATCAGCATCCATGTTG    3780
GAATTTAATCGCGGCCTCGACGAAGACGTTTCCCGTTGAATATGGCTCATAACACCCCTT    3840
GTATTACTGTTTATGTAAGCAGACAGTTTTATTGTTCATGATGATATATTTTTATCTTGT    3900
GCAATGTAACATCAGGGCCTCGTGATACGCCTATTTTTATAGGTTAATGTCATGATAATA    3960
```

Figure 15 cont'd...

```
ATGGTTTCTTAGACGTGAGGTTCTGTACCCGACACCATCGAATGGTGCAAAACCTTTCGC      4020
GGTATGGCATGATAGCGCCCGGAAGAGAGTCAATTCAGGGTGGTGAATGTGAAACCAGTA      4080
ACGTTATACGATGTCGCAGAGTATGCCGGTGTCTCTTATCAGACCGTTTCCCGCGTGGTG      4140
AACCAGCCCAGCCACGTTTCTGCGAAAACGCGGGAAAAAGTGGAAGCGCCGATGGCGGAG      4200
CTGAATTACATTCCCAACCGCGTGGCACAACAACTGCCGGGCAAACAGTCGTTGCTGATT      4260
GGCGTTGCCACCTCCAGTCTGGCCCTGCACGCGCCGTCGCAAATTGTCGCCGCGATTAAA      4320
TCTCGCGCCGATCAACTGGGTGCCAGCGTGGTGGTCTCGATGGTAGAACGAAGCGGCGTC      4380
GAAGCCTGTAAAGCGGCGGTGCACAATCTTCTCGCGCAACGCGTCAGTGGGCTGATCATT      4440
AACTATCCGCTGGATGACCAGGATGCCATTGCTGTGGAAGCTGCCTGCACTAATGTTCCG      4500
GCGTTATTTCTTGATGTCTCTGACCAGACACCCATCAACAGTATTATTTTCTCCCATGAA      4560
GACGGTACGCGACTGGGCGTGGAGCATCTGGTCCCATTGGGTCACCAGCAAATCGCGCTG      4620
TTAGCGGGCCCATTAAGTTCTGTCTCGGCGCGTCTGCGTCTGGCTGGCTGGCATAAATAT      4680
CTCACTCGCAATCAAATTCAGCCGATAGCGGAACGGGAAGGCGACTGGAGTGCCATGTCC      4740
GGTTTTCAACAAACCATGCAAATGCTGAATGAGGGCATCGTTCCCACTGCGATGCTGGTT      4800
GCCAACGATCAGATGGCGCTGGGCGCAATGCGCGCCATTACCGAGTCCGGGCTGCGCGTT      4860
GGTGCGGATATCTCGGTAGTGGGATACGACGATACCGAAGACAGCTCATGTTATATCCCG      4920
CCGTTAACCACCATCAAACAGGATTTTCGCCTGCTGGGGCAAACCAGCGTGGACCGCTTG      4980
CTGCAACTCTCTCAGGGCCAGGCGGTGAAGGGCAATCAGCTGTTGCCCGTCTCACTGGTG      5040
AAAAGAAAAACCACCCTGGCGCCCAATACGCAAACCGCCTCTCCCCGCGCGTTGGCCGAT      5100
TCATTAATGCAGCTGGCACGACAGGTTTCCCGACTGGAAAGCGGGCAGTGAGCGCAACGC      5160
AATTAATGTAAGTTAGCTCACTCATTAGGCACCCCAGGCTTTACACTTTATGCTTCCGAC      5220
CTGCAAGAACCTCACGTCAGGTGGCACTTTTCGGGGAAATGTGCGCGGAACCCCTATTTG      5280
TTTATTTTTCTAAATACATTCAAATATGTATCCGCTCATGAGACAATAACCCTGATAAAT      5340
GCTTCAATAATATTGAAAAAGCAAGAGTATGAGTATTCAACATTTCCGTGTCGCCCTTAT      5400
TCCCTTTTTTGCGGCATTTTGCCTTCCTGTTTTTGCTCACCCAGAAACGCTGGTGAAAGT      5460
AAAAGATGCTGAAGATCAGTTGGGTGCACGAGTGGGTTACATC   5503
```

Figure 16 pTTQ18NHK sequence containing PPase (bold) and remainder of PCR product cloned (italics) (SEQ ID NO 13)

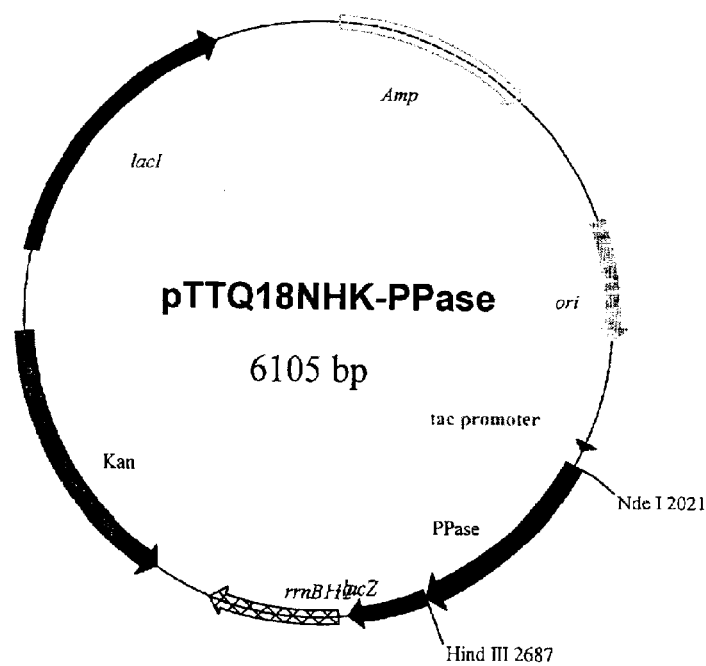

Figure 16 cont'd...

```
>PTTQ18NHK-PPASE SEQUENCE
GAACTGGATCTCAACAGCGGTAAGATCCTTGAGAGTTTTCGCCCCGAAGAACGTTTTCCA      60
ATGATGAGCACTTTTAAAGTTCTGCTATGTGGCGCGGTATTATCCCGTATTGACGCCGGG     120
CAAGAGCAACTCGGTCGCCGCATACACTATTCTCAGAATGACTTGGTTGAGTACTCACCA     180
GTCACAGAAAAGCATCTTACGGATGGCATGACAGTAAGAGAATTATGCAGTGCTGCCATA     240
ACCATGAGTGATAACACTGCGGCCAACTTACTTCTGACAACGATCGGCAGGACCGAAGGAG     300
CTAACCGCTTTTTTGCACAACATGGGGGATCATGTAACTCGCCTTGATCGTTGGGAACCG     360
GAGCTGAATGAAGCCATACCAAACGACGAGCGTGACACCACGATGCCTGTAGCAATGGCA     420
ACAACGTTGCGCAAACTATTAACTGGCGAACTACTTACTCTAGCTTCCCGGCAACAATTA     480
ATAGACTGGATGGAGGCGGATAAAGTTGCAGGACCACTTCTGCGCTCGGCCCTTCCGGCT     540
GGCTGGTTTATTGCTGATAAATCTGGAGCCGGTGAGCGTGGGTCTCGCGGTATCATTGCA     600
GCACTGGGGCCAGATGGTAAGCCCTCCCGTATCGTAGTTATCTACACGACGGGGAGTCAG     660
GCAACTATGGATGAACGAAATAGACAGATCGCTGAGATAGGTGCCTCACTGATTAAGCAT     720
TGGTAACTGTCAGACCAAGTTTACTCATATATACTTTACATTGATTTAAAACTTCATTTT     780
TAATTTAAAAGGATCTAGGTGAAGATCCTTTTTGATAATCTCATGACCAAAATCCCTTAA     840
CGTGAGTTTTCGTTCCACTGAGCGTCAGACCCCGTAGAAAAGATCAAAGGATCTTCTTGA     900
GATCCTTTTTTTCTGCGCGTAATCTGCTGCTTGCAAACAAAAAAACCACCGCTACCAGCG     960
GTGGTTTGTTTGCCGGATCAAGAGCTACCAACTCTTTTTCCGAAGGTAACTGGCTTCAGC    1020
AGAGCGCAGATACCAAATACTGTCCTTCTAGTGTAGCCGTAGTTAGGCCACCACTTCAAG    1080
AACTCTGTAGCACCGCCTACATACCTCGCTCTGCTAATCCTGTTACCAGTGGCTGCTGCC    1140
AGTGGCGATAAGTCGTGTCTTACCGGGTTGGACTCAAGACGATAGTTACCGGATAAGCCG    1200
CAGCGGTCGGGCTGAACGGGGGGTTCGTGCACACAGCCCAGCTTGGAGCGAACGACCTAC    1260
ACCGAACTGAGATACCTACAGCGTGAGCATTGAGAAAGCGCCACGCTTCCCGAAGGGAGA    1320
AAGGCGGACAGCTATCCGGTAAGCGGCAGGGTCGGAACAGGAGAGCGCACGAGGGAGCTT    1380
CCAGGGGGAAACGCCTGGTATCTTTATAGTCCTGTCGGGTTTCGCCACCTCTGACTTGAG    1440
CGTCGATTTTTGTGATGCTCGTCAGGGGGCGGAGCCTATGGAAAAACGCCAGCAACGCG    1500
GCCTTTTTACGGTTCCTGGCCTTTTGCTGGCCTTTTGCTCACATGTTCTTTCCTGCGTTA    1560
TCCCCTGATTCTGTGGATAACCGTATTACCGCCTTTGAGTGAGCTGATACCGCTCGCCGC    1620
AGCCGAACGACCGAGCGCAGCGAGTCAGTGAGCGAGGAAGCGGAAGAGCGCCCAATACGC    1680
AAACCGCCTCTCCCCGCGCGTTGGCCGATTCATTAATGCAGAATTAATTCTCATGTTTGA    1740
CAGCTTATCATCGACTGCACGGTGCACCAATGCTTCTGGCGTCACGCAGCCATCGGAAGC    1800
TGTGGTATGGCTGTGCAGGTCGTAAATCACTGCATAATTCGTGTCGCTCAAGGCGCACTC    1860
CCGTTCTGGATAATGTTTTTTGCGCCGACATCATAACGGTTCTGGCAAATATTCTGAAAT    1920
GAGCTGTTGACAATTAATCATCGGCTCGTATAATGTGTGGAATTGTGAGCGGATAACAAT    1980
TTCACACAGGAAACACATATATGCACCACCACCACCACCATATGACAGGCTGTCTGAAAA    2040
TTGGTCCTGGAGATGAGGCTCCAGATGTTGTGAATGTCGTTATAGAGATACCTATGAACA    2100
GTTCTGTTAAGTACGAGTTCGACAAGGAGGCGTGTATTGTTAAGGTTGATAGGTTCCTTT    2160
ACACCAGCATGGTCTACCCCTTCAACTACGGGTTCATACCAGGCACTCTAGAGGAGGACG    2220
GAGATCCTGTTGACGTTCTAGTTATTAGCCGGGAGCCCGTTGCTCCCGGCTCGCTTATAG    2280
AGGCTGTGCCCGTGGCCGTGTTAGACATGGAGGACGAGGAGGGTCCGGACAGCAAGGTTG    2340
TTGCCGTACCCAAGGCCAAGCTGGACCCCCTATTCGCCAGCTATAAGGACGTTGGCGACA    2400
TACCTGATGCCCTGAAATCCAAGATAAAGCACTTCTTCGAGCACTATAAGGAGCTGGAGC    2460
CTGGAAAGTGGGTTAGAGTGACTGGATGGAGGCCTGCTGCCGATGCGAAGGAGATTATAA    2520
GGAGGGCTATAGAGAGGTATAAGGGGGCGTGATGAGGCTTAACCGCTCACGTTTTCTGG    2580
GAGAGTGTCGCACCTTTGAGGGCGATCACCCTCGCCAGCGTGCGTGTGCTTTTGTCTATG    2640
ATTATGGCTACAGTTCTTCTAGCCGCTTTCACCGCCCCACAGTCAACCTTGGCACTGGC    2700
CGTCGTTTTACAACGTCGTGACTGGGAAAACCCTGGCGTTACCCAACTTAATCGCCTTGC    2760
AGCACATCCCCCTTTCGCCAGCTGGCGTAATAGCGAAGAGGCCCGCACCGATCGCCCTTC    2820
CCAACAGTTGCGCAGCCTGAATGGCGAATGGCGCCTGATGCGGTATTTTCTCCTTACGCA    2880
TCTGTGCGGTATTTCACACCGCATAAATTCCCTGTTTTGGCGGATGAGAGAAGATTTTCA    2940
GCCTGATACAGATTAAATCAGAACGCAGAAGCGGTCTGATAAAACAGAATTTGCCTGGCG    3000
GCAGTAGCGCGGTGGTCCCACCTGACCCCATGCCCAACTCAGAAGTGAAACGCCGTAGCG    3060
CCGATGGTAGTGTGGGGTCTCCCCATGCGAGAGTAGGGAACTGCCAGGCATCAAATAAAA    3120
CGAAAGGCTCAGTCGAAAGACTGGGCCTTTCGTTTTATCTGTTGTTTGTCGGTGAACGCT    3180
CTCCTGAGTAGGACAAATCCGCCGGGAGCGGATTTGAACGTTGCGAAGCAACGGCCCGGA    3240
GGGTGGCGGGCAGGACCCCCGCCATAAACTGCCAGGCATCAAATTAAGCAGAAGGCCATC    3300
CTGACGGATGGCCTTTTTGCGTTTCTACAAACTCTTCCTGTCGTCATATCTACAAGCCAT    3360
CCCCCCACAGATACGGTAAACTAGCCTCGTTTTTGCATCAGGAAAGCAGGGAATTTATGG    3420
TGCACTCTCAGTACAATCTGCTCTGATGCCGCATAGTTAAGCCAGCCCCGACACCCGCCA    3480
ACACCCGCTGACGCGCCCTGACGGGCTTGTCTGCTCCCGGCATCCGCTTACAGACAAGCT    3540
GTGACCGTCTCCGGGAGCTGCATGTGTCAGAGGTTTTCACCGTCATCACCGAAACGCGCG    3600
AGACGAAAGGGCCTGATTAGAAAAACTCATCGAGCATCAAATGAAACTGCAATTTATTCA    3660
```

Figure 16 cont'd...

```
TATCAGGATTATCAATACCATATTTTTGAAAAAGCCGTTTCTGTAATGAAGGAGAAAACT      3720
CACCGAGGCAGTTCCATAGGATGCCAAGATCCTGGTATCGGTCTGCGATTCCGACTCGTC      3780
CAACATCAATACAACCTATTAATTTCCCCTCGTCAAAAATAAGGTTATCAAGTGAGAAAT      3840
CACCATGAGTGACGACTGAATCCGGTGAGAATGGCAAAAGNTTATGCATTTCTTTCCAGA      3900
CTTGTTCAACAGGCCAGCCATTACGCTCGTCATCAAAATCACTCGCATCAACCAAACCGT      3960
TATTCATTCGTGATTGCGCCTGAGCGAGACGAAATACGCGATCGCTGTTAAAAGGACAAT      4020
TACAAACAGGAATCGAATGCAACCGGCGCAGGAACACTGCCAGCGCATCAACAATATTTT      4080
CACCTGAATCAGGATATTCTTCTAATACCTGGAATGCTGTTTTCCCNGGGATCGCAGTGG      4140
TGAGTAACCATGCATCATCAGGAGTACGGATAAAATGCTTGATGGTCGGAAGAGGCATAA      4200
ATTCCGTCAGCCAGTTTAGTCTGACCATCTCATCTGTAACATCATTGGCAACGCTACCTT      4260
TGCCATGTTTCAGAAACAACTCTGGCGCATCCGCTTCCCATACAATCGATAGATTGTCG      4320
CACCTGATTGCCCGACATTATCGCGAGCCCATTTATACCCATATAAATCAGCATCCATGT      4380
TGGAATTTAATCGCGGCCTCGAGCAAGACGTTTCCCGTTGAATATGGCTCATAACACCCC      4440
TTGTATTACTGTTTATGTAAGCAGACAGTTTTATTGTTCATGATGATATATTTTTATCTT      4500
GTGCAATGTAACATCAGGGCCTCGTGATACGCCTATTTTTATAGGTTAATGTCATGATAA      4560
TAATGGTTTCTTAGACGTGAGGTTCTGTACCCGACACCATCGAATGGTGCAAAACCTTTC      4620
GCGGTATGGCATGATAGCGCCCGGAAGAGAGTCAATTCAGGGTGGTGAATGTGAAACCAG      4680
TAACGTTATACGATGTCGCAGAGTATGCCGGTGTCTCTTATCAGACCGTTTCCCGCGTGG      4740
TGAACCAGCCAGCCACGTTTCTGCGAAAACGCGGGAAAAAGTGGAAGCGGCGATGGCGC      4800
AGCTGAATTACATTCCCAACCGCGTGGCACAACAACTGGCGGGCAAACAGTCGTTGCTGA      4860
TTGGCGTTGCCACCTCCAGTCTGGCCCTGCACGCGCCGTCGCAAATTGTCGCGGCGATTA      4920
AATCTCGCGCCGATCAACTGGGTGCCAGCGTGGTGGTGTCGATGGTAGAACGAAGCGGCG      4980
TCGAAGCCTGTAAAGCGGCGGTGCACAATCTTCTCGCGCAACGCGTCAGTGGGCTGATCA      5040
TTAACTATCCGCTGGATGACCAGGATGCCATTGCTGTGGAAGCTGCCTGCACTAATGTTC      5100
CGGCGTTATTTCTTGATGTCTCTGACCAGACACCCATCAACAGTATTATTTTCTCCCATG      5160
AAGACGGTACGCGACTGGGCGTGGAGCATCTGGTCGCATTGGGTCACCAGCAAATCGCGC      5220
TGTTAGCGGGCCCATTAAGTTCTGTCTCGGCGCGTCTGCGTCTGCTGGCTGGCATAAAT      5280
ATCTCACTCGCAATCAAATTCAGCCGATAGCGGAACGGGAAGGCGACTGGAGTGCCATGT      5340
CCGGTTTTCAACAAACCATGCAAATGCTGAATGAGGGCATCGTTCCCACTGCGATGCTGG      5400
TTGCCAACGATCAGATGGCGCTGGGCGCAATGCGCGCCATTACCGAGTCCGGGCTGCGCG      5460
TTGGTGCGGATATCTCGGTAGTGGGATACGACGATACCGAAGACAGCTCATGTTATATCC      5520
CGCCGTTAACCACCATCAAACAGGATTTTCGCCTGCTGGGGCAAACCAGCGTGGACCGCT      5580
TGCTGCAACTCTCTCAGGGCCAGGCGGTGAAGGGCAATCAGCTGTTGCCCGTCTCACTGG      5640
TGAAAAGAAAAACCACCCTGGCGCCCAATACGCAAACCGCCTCTCCCCGCGCGTTGGCCG      5700
ATTCATTAATGCAGCTGGCACGACAGGTTTCCGACTGGAAAGCGGGCAGTGAGCGCAAC      5760
GCAATTAATGTAAGTTAGCTCACTCATTAGGCACCCCAGGCTTTACACTTTATGCTTCCG      5820
ACCTGCAAGAACCTCACGTCAGGTGGCACTTTTCGGGGAAATGTGCGCGGAACCCCTATT      5880
TGTTTATTTTTCTAAATACATTCAAATATGTATCCGCTCATGAGACAATAACCCTGATAA      5940
ATGCTTCAATAATATTGAAAAAGGAAGAGTATGAGTATTCAACATTTCCGTGTCGCCCTT      6000
ATTCCCTTTTTTGCGGCATTTTGCCTTCCTGTTTTTGCTCACCCAGAAACGCTGGTGAAA      6060
GTAAAAGATGCTGAAGATCAGTTGGGTGCACGAGTGGGTTACATC                     6105
```

AMPLIFICATION PROCESS

This application claims priority to Great Britain Application No. 0110501.4 filed on Apr. 30, 2001, the entire contents of which are incorporated herein by reference.

The present invention relates to processes for carrying out reactions in which nucleic acids are amplified, to means of controlling these reactions and kits and reagents, in particular enzymes, used for conducting them.

Amplification reactions such as the polymerase chain reaction (PCR) are very well known and widely used in the fields of biotechnological research, as well as in diagnostics and detection.

PCR is a procedure for generating large quantities of a particular nucleic acid sequence, in particular a DNA sequence, and is based upon DNA's characteristics of base pairing and precise copying of complementary DNA strands. Typical PCR involves a cycling process of three basic steps.

Denaturation: A mixture containing the PCR reagents (including the nucleic acid to be copied, which may be DNA or RNA (the template), the individual nucleotide bases (A,T,G,C), suitable primers and polymerase enzyme) are heated to a predetermined temperature to separate the two strands of the target DNA.

Annealing: The mixture is then cooled to another predetermined temperature and the primers locate their complementary sequences on the DNA strands and bind to them.

Extension: The mixture is heated again to a further predetermined temperature. The polymerase enzyme (acting as a catalyst) joins the individual nucleotide bases to the end of the primer to form a new strand of DNA which is complementary to the sequence of the target DNA, the two strands being bound together.

Such reactions rely on the sequence of steps occurring in a very precise order and at the precise temperature required for the operation of that step. A problem arises when reagents are mixed together, even for short periods of time, at different temperatures, for example prior to the start of the reaction. Primers may interact with nucleic acid template, resulting in primer extension of the template. This can lead to a reduction in the overall yield of the desired product as well as the production of non-specific products.

Various means of overcoming this problem have been proposed previously. For example, initial attempts to overcome the problem used a wax barrier to separate the various PCR reagents from each other in a test tube (see for example U.S. Pat. No. 5,565,339). The wax melted as the reaction mixture was heated to the initial denaturation temperature, allowing the reagents to mix together at the last possible moment, so that the possibility of side-reactions was minimised. Such reactions are known as "Hot Start" reactions.

Other chemical methods for achieving the suppression of side-reactions have been attempted. For example, U.S. Pat. No. 5,677,152 describes a method in which the DNA polymerase is chemically modified to ensure that it only becomes active at elevated temperatures. In order to carry out this method however, it is necessary to incubate the reaction mixture at high temperatures for some time in order to generate active enzyme. Such delays, whilst not significant in some instances, can be detrimental where the results of PCR are required rapidly. For many applications of the PCR technique it is desirable to complete the sequence of cycles in the minimum possible time. In particular for example where respiratory air or fluids or foods for human and animal stock consumption are suspected of contamination rapid diagnostic methods may save considerable money if not health, even lives.

In other methods, a monoclonal antibody to *Thermus aquaticus* (Taq) DNA polymerase such as the anti-Taq DNA polymerase antibody available from Sigma, is introduced into the reaction mixture. The antibody binds to the enzyme, so as to inactivate it, at ambient temperature. However, the antibody denatures and dissociates from the enzyme at elevated temperatures used during the amplification cycles and so the enzyme becomes active. The method however does not appear to eliminate non-specific side-products in some cases.

Primer extension of a template during a PCR reaction can be represented as:

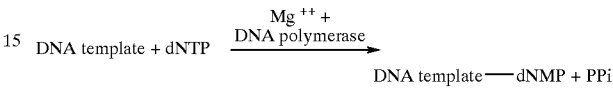

where dNTP is a deoxyribonucleic acid triphosphates, dNMP is the corresponding deoxyribonucleic acid monophosphate and PPi is an inorganic pyrophosphate. This reaction may also be represented as

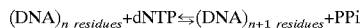

The presence of increased levels of PPi, for example in a DNA sequencing reaction is known to force the reaction shown above in reverse. This is known as pyrophosphorolysis and it is a recognised problem in DNA sequencing at 70° C. using thermostable DNA polymerases. It has been overcome through the addition of a thermostable PPase to the DNA polymerase formulation used in DNA sequencing.

The applicants have found that this reaction can form the basis of an advantageous amplification reaction in which the production of non-specific products may be minimised.

According to the present invention there is provided a method for conducting a nucleic acid amplification reaction, said method comprising forming an amplification reaction mixture in the presence of a pyrophosphate salt to prevent primer extension taking place, enzymatically digesting said pyrophosphate, and subjecting said reaction mixture to conditions such that an amplification reaction may proceed.

Using the method of the invention, accurate amplification reactions, which may be carried out rapidly and with good specificity, can be carried out. It therefore represents a good alternative to existing "Hot Start" amplification technologies.

The initial amplification reaction mixture used in the method of the invention is broadly speaking, a conventional mixture, such as that used in the PCR reaction, to which pyrophosphate salt is added. Thus it will generally comprise: i) a sample which contains or is suspected of containing a target nucleic acid sequence, (ii) at least one primer which hybridises to an end region of said target sequence, iii) a source of magnesium ions, (iv) nucleotide or nucleoside bases which constitute the target sequence (i.e. A, T, C, G and/or U in the case of DNA amplification or A,U,C and G in the case of RNA amplification), and (v) a DNA polymerase which is thermostable at the temperatures at which the amplification reaction is effected. It will also comprise a buffer, as necessary in order to effect the reaction, as is known in the art.

In particular (iv) will comprise nucleotides A, T, G and C in respect of DNA amplification and nucleosides A, U, C and G in respect of RNA amplification.

Other combinations may be used however, where other primer based amplifications reactions such as reverse transcriptase PCR (RT-PCR) are being conducted.

In addition, the reagents may include labelled probes or primers, and/or other labelling means such as intercalating dyes such as Sybr Green, Sybr Gold, ethidium bromide etc. or combinations of these, which might allow the application to be monitored, without the need to examine the product on a gel subsequently. The nature of these depends upon the type of assay being undertaken. Generic intercalator methods use intercalating dyes to monitor the increase in double stranded DNA which occurs during an amplification process. These are only quasi-strand-specific and therefore other labels are required where strand specific detection is required.

Strand specific methods utilise additional nucleic acid reaction components to monitor the progress of amplification reactions. These methods often use fluorescence energy transfer (FET) as the basis of detection. One or more nucleic acid probes are labelled with fluorescent molecules, one of which is able to act as an energy donor and the other of which is an energy acceptor molecule. These are sometimes known as a reporter molecule and a quencher molecule respectively. The donor molecule is excited with a specific wavelength of light which falls within its excitation spectrum and subsequently it will emit light within its fluorescence emission wavelength. The acceptor molecule is also excited at this wavelength by accepting energy from the donor molecule by a variety of distance-dependent energy transfer mechanisms. A specific example of fluorescence energy transfer which can occur is Fluorescence Resonance Energy Transfer or "FRET". Generally, the acceptor molecule accepts the emission energy of the donor molecule when they are in close proximity (e.g. on the same, or a neighbouring molecule). The basis of fluorescence energy transfer detection is to monitor the changes at donor and acceptor emission wavelengths.

There are two commonly used types of FET or FRET probes, those using hydrolysis of nucleic acid probes to separate donor from acceptor, and those using hybridisation to alter the spatial relationship of donor and acceptor molecules.

Hydrolysis probes are commercially available as TaqMan™ probes. These consist of DNA oligonucleotides that are labelled with donor and acceptor molecules. The probes are designed to bind to a specific region on one strand of a PCR product.

Following annealing of the PCR primer to this strand, Taq enzyme extends the DNA with 5' to 3' polymerase activity. Taq enzyme also exhibits 5' to 3' exonuclease activity. TaqMan™ probes are protected at the 3' end by phosphorylation to prevent them from priming Taq extension. If the TaqMan™ probe is hybridised to the product strand, an extending Taq molecule may also hydrolyse the probe, liberating the donor from acceptor as the basis of detection. The signal in this instance is cumulative, the concentration of free donor and acceptor molecules increasing with each cycle of the amplification reaction.

U.S. Pat. No. 5,491,063 describes a method for in-solution quenching of fluorescently labelled probes which relies on modification of the signal from a labelled single stranded oligonucleotide by a DNA binding agent. The difference in this signal which occurs as a result of a reduced chain length of the probe following probe cleavage (hydrolysis) during a polymerase chain reaction is suggested for providing a means for detecting the presence of a target nucleic acid.

Hybridisation probes are available in a number of forms. Molecular beacons are oligonucleotides that have complementary 5' and 3' sequences such that they form hairpin loops. Terminal fluorescent labels are in close proximity for FRET to occur when the hairpin structure is formed. Following hybridisation of molecular beacons to a complementary sequence the fluorescent labels are separated, so FRET does not occur, and this forms the basis of detection.

Pairs of labelled oligonucleotides may also be used. These hybridise in close proximity on a PCR product strand bringing donor and acceptor molecules together so that FRET can occur. Enhanced FRET is the basis of detection. Variants of this type include using a labelled amplification primer with a single adjacent probe.

U.S. Pat. No. 4,868,103 describes in general terms, a FRET system for detecting the presence of an analyte, which utilises an intercalating dye as the donor molecule. The process does not involve an amplification stage.

Other examples of assays which utilise FET or FRET detection are described in WO 99/28500, which utilises a combination of an intercalating dye and a single labelled probe as a signalling system, WO 99/28501 which utilises a combination of a labelled primer and an enzyme to generate a detectable fluorescent signal, and WO 99/42611 which uses a combination of an intercalating dye and a fluorescently labelled nucleotide as the basis of the signal. Yet further assays which utilise complex primers including labels and chemical blocking agents and which are complementary are described for example in WO 99/66071.

Reaction mixtures used in the method of the invention may include any of the labelling reagents necessary to conduct assays as described above. In particular, such reaction mixtures may advantageously be used in genotyping and, more especially, in SNP evaluation. In these instances, the method of the present invention is used in combination with dual Taqman™ probes, one specific for the basic sequence and one specific for the mutant. Each probe preferably contains a different flurophore and therefore different signals are generated depending on the amount of the various forms of the gene present. A single signal is generated from a homozygote and a mixed signal is generated from a heterozygote.

Examples of suitable DNA polymerases which may be used in the context of the invention are thermostable polymerases such as *Thermus aquaticus* polymerase (Taq), *Thermus thermophilus* polymerase (Tth), *Thermus* species NH polymerase (TspNH), *Thermus brockianus* polymerase (Tbr) (all obtainable for example from GeneSys Limited, Farnborough, U.K.), *Pyrococcus furiosus* polymerase (Pfu) (obtainable from Stratagene), 9°N7 exo-DNA polymerase, and *Thermococcus litoralis* DNA polymerase (obtainable from New England Biolabs as VENT™ DNA polymerase).

The pyrophosphate used in the method of the invention may be any soluble pyrophosphate including soluble metal and non-metal (e.g. ammonium salts). Such compounds are often generically known as "inorganic pyrophosphate" or PPi and this nomenclature is used in the present application. In particular, the pyrophosphate will be an alkali metal pyrophosphate, such as sodium or potassium pyrophosphates including disodium pyrophosphate ($Na_2H_2P_2O_7$), anhydrous tetrasodium pyrophosphate ($Na_4P_2O_7$), tetrasodium pyrophosphate decahydrate ($Na_4P_2O_7.10\ H_2O$) and tetrapotassium pyrophosphate (anhydrous). Other soluble pyrophosphates which may be used include iron pyrophosphates such as ferric pyrophosphate ($Fe_4(P_2O_7)_3$), and soluble ammonium salts such as anhydrous tributylammonium pyrophosphate. Other soluble pyrophosphates are available from commercial sources.

A preferred inorganic pyrophosphate is tetrasodium pyrophosphate of formula $Na_4P_2O_7$.

The concentration of pyrophosphate used in the reaction mixture should be sufficient to prevent primer extension taking place. This will depend to a large extent upon the particular nature and concentration of the sequences being amplified, the primers and the polymerase enzymes being used, as well as their concentrations, and may be determined in any particular case by routine methods.

The reaction mixture formed initially suitably contains pyrophosphate at a concentration of at least 0.5 mM, suitably at a concentration of least 1 mM, for example from 1–10 mM and preferably from 1–5 mM.

Enzymatic digestion of the inorganic pyrophosphate is suitably effected immediately prior to or during first phase of the amplification reaction. This may be achieved by addition of an pyrophosphatase enzyme (PPase) (which may be known as an inorganic pyrophosphatase enzyme—PPiase) immediately prior to the start of the amplification reaction.

Preferably, however, the enzymatic digestion is effected using a thermostable PPase, which is active at elevated temperatures, for example at temperatures in excess of 50° C. Preferably the enzyme is only significantly active at these elevated temperatures. This means that the PPase may be included in the reaction mixture on formation, but it will not or not significantly digest the inhibitory pyrophosphate at ambient temperature. It will only become properly active when the reaction mixture is heated as will be necessary for example during the initial denaturation phase of a PCR reaction. However, a short preliminary incubation at elevated temperature, for example at from 50 to 100° C., and, preferably, at from 80 to 95° C., may be carried out.

Examples of thermostable PPase include *Sulfolbus acidicaldarius* pyrophosphatase, (Sac PPase—Meyer et al. Achives of Biochem. and Biophys. (1995) 319, 1, 149–156) obtainable from GeneSys Limited, Farnborough UK., or *Thermococcus litoralis* pyrophosphatase, available from New England Biolabs (Catalogue nos #M0296S and #M0296L). Preferably the thermostable PPase is *Aeropyrum pernix* inorganic pyrophosphatase obtainable from Genesys Limited, Farnborough UK.

*Aeropyrum pernix* K1, the first strictly aerobic hyperthermophilic archeaon, was isolated in 1993 from a coastal solfataric thermal vent at Kodaka ra-Jima Island, Japan, (Sako et al, Int. J. Syst. Bacteriol. 46 (1996): 1070–1077. It is deposited in the Japan Collection of Microorganisms, JCM 9820.

The applicants have for the first time isolated a thermostable PPase from *Aeropyrum pernix* and this forms a further aspect of the present invention. The genomic sequence comprising this pyrophosphatase is shown in SEQ ID NO. 1 and the corresponding amino acid sequence is shown in SEQ ID NO. 2 (FIG. 11 hereinafter). In particular the enzyme of the invention has the amino acid sequence as shown as SEQ ID NO 25, which is encoded by the region of SEQ ID NO 1 shown in bold type in FIG. 11, and represented also as SEQ ID NO 26.

The present invention, therefore, includes a polynucleotide comprising SEQ ID NO 26 and variants or fragments thereof. For example, the invention provides a polynucleotide of SEQ ID NO 1.

The present invention further includes an amino acid sequence comprising SEQ ID NO 25 and variants or fragments thereof. For example, the amino acid sequence may comprise SEQ ID NO 2.

The term "fragment thereof" as used herein in relation to a polynucleotide sequence refers to any portion of the given polynucleotide sequence which has the same activity as the complete polynucleotide sequence. Fragments will suitably comprise at least 300 and preferably at least 450 consecutive bases from the basic sequence.

The term "variant thereof" in relation to a polynucleotide sequences means any substitution of, variation of, modification of, replacement of deletion of, or the addition of one or more nucleic acid(s) from or to a polynucleotide sequence providing the resultant protein sequence encoded by the polynucleotide exhibits the same properties as the protein encoded by the basic sequence. The term therefore includes allelic variants and also includes a polynucleotide which substantially hybridises to the polynucleotide sequence of the present invention. Preferably, such hybridisation occurs at, or between low and high stringency conditions. In general terms, low stringency conditions can be defined as 3×SSC at about ambient temperature to about 55° C. and high stringency condition as 0.1×SSC at about 65° C. SSC is the name of the buffer of 0.15M NaCl. 0.015M tri-sodium citrate. 3×SSC is three times as strong as SSC and so on.

Typically, variants have 62% or more of the nucleotides in common with the polynucleotide sequence of the present invention, more typically 65%, preferably 70%, even more preferably 80% or 85% and, especially preferred are 90%, 95%, 98% or 99% or more identity.

When comparing nucleic acid sequences for the purposes of determining the degree of identity, programs such as BESTFIT and GAP (both from Wisconsin Genetics Computer Group (GCG) software package). BESTFIT, for example, compares two sequences and produces an optimal alignment of the most similar segments. GAP enables sequences to be aligned along their whole length and fins the optimal alignment by inserting spaces in either sequence as appropriate. Suitably, in the context of the present invention when discussing identity of nucleic acid sequences, the comparison is made by alignment of the sequences along their whole length.

The term "fragment thereof" as used herein in relation to an amino acid sequence refers to any portion of the given amino acid sequence which has the same activity as the complete amino acid sequence. Fragments will suitably comprise at least 100 and preferably at least 150 consecutive amino acids from the basic sequence.

The term "variant thereof" as used herein in relation to an amino acid sequence means sequences of amino acids which differ from the base sequence from which they are derived in that one or more amino acids within the sequence are substituted for other amino acids. Amino acid substitutions may be regarded as "conservative" where an amino acid is replaced with a different amino acid with broadly similar properties. Non-conservative substitutions are where amino acids are replaced with amino acids of a different type. Broadly speaking, fewer non-conservative substitutions will be possible without altering the biological activity of the polypeptide. Suitably variants will be at least 60% identical, preferably at least 75% identical, and more preferably at least 90% identical to the base sequence.

Homology in this instance can be judged for example using the algorithm of Lipman-Pearson, with Ktuple:2, gap penalty:4, Gap Length Penalty:12, standard PAM scoring matrix (Lipman, D. J. and Pearson, W. R., Rapid and Sensitive Protein Similarity Searches, *Science*, 1985, vol. 227, 1435–1441).

Preferably, the polynucleotide of the present invention comprises SEQ ID NO 26 and sequences having greater than 62% identity thereto.

These enzymes may be obtained from the natural source, or may be expressed in recombinant host cells, such as *E. coli* cells, using conventional methods.

Removal of pyrophosphate for example, at >50° C. by the action of a thermostable pyrophosphatase enzyme (PPase) then allows primer extension (and therefore amplification) to proceed as normal. During this process, 1 mole of pyrophosphate is converted to 2 moles of inorganic phosphate (Pi), which does not interfere with the amplification reaction.

The amount of pyrophosphatase included should be sufficient to digest excess pyrophosphate salt present in the reaction mixture. Generally speaking, this will be greater than the amounts of these enzymes used conventionally in an equivalent cycle reaction to prevent pyrophosphorolysis, for example some 5 fold more. The precise amounts will depend upon various factors including the particular enzyme being used, the concentration of the pyrophosphate etc. Typically, PPase and particularly thermostable PPase enzymes will be included in the amplification reaction mixture at concentrations of at least 0.04 units per 50 µL PCR reaction mixture, preferably at least 0.08 units per 50 µL PCR reaction mixture and more preferably from about 0.2–10 units per 50 µL PCR reaction mixture. In this case, one unit is defined as the amount of enzyme catalysing the conversion of 1 µmol pyrophosphate into 2 µmol orthophosphate in one minute at 75° C. under the following reaction conditions: 1 mM $K_4P_2O_7$, 2 mM $MgCl_2$, 50 mM Tris-HCl, pH 9.0 (25° C.).

Enzymes used in the method of the invention can result in rapid removal of inorganic pyrophosphate, depending upon the temperature being used. Generally complete removal can be achieved in less than 5 minutes, more often, in less than 2 minutes and as little as 15 seconds if required.

Once the inorganic pyrophosphate has been enzymatically removed from the reaction mixture, the amplification reaction can proceed, for example using a conventional thermal cycling procedure.

The mechanism by which the method of the invention achieves the desired result is not clear. It is probable that the presence of excess pyrophosphate inhibits the primer extension reaction. There appears, however, to be no noticeable decrease in PCR sensitivity or product yield.

The method of the invention can be conducted in any conventional apparatus for conducting application reactions. These include conventional block heating devices as described for example in EP-A-0810030 and supplied by The Perkin-Elmer Corporation, or rapid hot air thermal cyclers such as the RapidCycler™ and LightCycler™ from Idaho Technologies Inc. or other types of thermal cycler such as those described in WO98/24548.

According to a further aspect, the invention provides a kit for conducting an amplification reaction, said kit comprising an inorganic pyrophosphate, an inorganic pyrophosphatase enzyme, and optionally one or more reagents required for use in an amplification reaction. The inorganic pyrophosphate is suitably present in a sufficient amount to inhibit an amplification reaction, as described above. Preferably the amount of inorganic pyrophosphatase enzyme present in the kit is sufficient to digest all of the said inorganic pyrophosphate.

The one or more reagents include any one of reagents (ii) to (v) listed above, and may also include buffers. Particular examples of inorganic pyrophosphatase enzymes are thermostable inorganic pyrophosphatase enzymes as described above.

In particular, the kits may suitably comprise as an optional additional reagent, one or more primers required to conduct amplification of a particular target DNA sequence, for example, a sequence, which is diagnostic of a particular disease condition or the presence of a particular pathogen in a sample. The methods may also be used in the detection of polymorphisms or allelic variations in genetic analysis.

Furthermore, the kits may comprise one or more labelled reagents such as intercalating dyes, or fluorescently labelled probes, primers or nucleotides, which may be useful in detecting or monitoring the amplification reaction in situ.

In a further aspect, the invention provides the use of an inorganic pyrophosphate as described above, in a method for carrying out amplification reactions as described above. Preferably, the inorganic pyrophosphatase enzyme is from *Aeropyrum pernix*.

Finally, in yet a further aspect, the invention provides the use of an inorganic pyrophosphatase enzyme as described above, in a method for carrying out amplification reactions as described above.

The invention will now be particularly described by way of example with reference to the accompanying diagrammatic drawings in which FIG. 1 shows the results of conducting a PCR in the presence of various amounts of PPi where PPi is tetrasodium pyrophosphate;

FIG. 11 shows the genomic sequence of *Aeropyrum pernix* shown as SEQ ID NO. 1 (Referenced as NC 000854 in GenBank BA000002), the corresponding amino acid sequence SEQ ID NO.2 and the sequence of the enzyme (SEQ ID NO 25);

FIG. 12 shows an alignment of different PPase sequences (SEQ ID NOS 2 to 9), including the protein sequence of *Aeropyrum pernix* shown as SEQ ID NO. 2;

FIG. 13 shows the 686 base pair PCR product (SEQ ID NO 10) produced during isolation of the pyrophosphatase enzyme from *Aeropyrum pernix;*

FIG. 14 shows the polylinker sequence (SEQ ID NO 11) used in the isolation of the pyrophosphatase from *Aeropyrum pernix;*

FIG. 15 shows the sequence of the pTTQ18NHK vector (SEQ ID NO 12) used in the isolation of the pyrophosphatase from *Aeropyrum pernix;*

FIG. 16 shows the sequence of the pTTQ18NHK vector including the PPase sequence used in the isolation of the pyrophosphatase from *Aeropyrum pernix* (SEQ ID NO 13)

EXAMPLE 1

Effect of PPi on PCR

Using Taq DNA polymerase, a standard 500 bp lambda template PCR using the following reagents, was conducted in the presence of differing quantities of the inorganic pyrophosphate, tetrasodium pyrophosphate decahydrate (PPi).

| Reagent | Volume | Final concn. |
| --- | --- | --- |
| 10× Reaction Buffer | 5 µl | 1× |
| 25 mM MgCl$_2$ | 3 µl | 1.5 mM |
| 5 mM dNTPs | 2 µl | 200 µM |
| 5' primer (10 pm/µl) | 5 µl | 1 µM |
| 3' primer (10 pm/µl) | 5 µl | 1 µM |
| Template | 1 ng | Lambda DNA |
| DNA polymerase (5 u/µl) | 0.25 | 1.25 u |
| Water to Total volume | 50.0 µl | |

Lambda 500 bp Primer sequences

```
5' Primer
GAT GAG TCC GTG TCC GTA CAA CTG G    (SEQ ID NO 16)

3' Primer
GGT TAT CGA AAT CAG CCA CAG CGC C    (SEQ ID NO 17)
```

Figure 1:
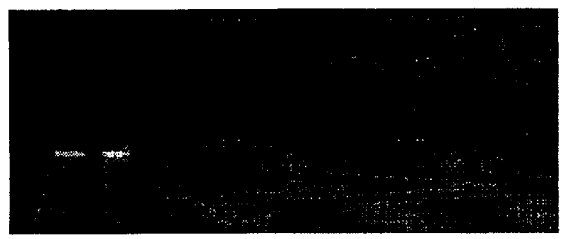

1×Reaction Buffer: 10 mM Tris. pH 8.0, 50 mM KCl. PCR conditions for the assay were as follows:

i) 94° C. 3.00 min ii) 20 cycles of 94° C. for 10 secs
   50° C. for 10 secs
   72° C. for 30 secs iii) 72° C. for 7 mins iv) 25° C. hold, The PPi was added such that the final concentration in the reaction mixture was 0, 1, 2, 3, 4 and 5 mM. The results are shown in FIG. 1. In this Figure, the lanes correspond to the following concentrations of PPi

| Lanes | |
| --- | --- |
| 1 + 2 | 0 PPi |
| 3 + 4 | 1 mM PPi |
| 5 + 6 | 2 mM PPi |
| 7 + 8 | 3 mM PPi |
| 9 + 10 | 4 mM PPi |
| 11 | 5 mM PPi |

At all levels of PPi tested, no PCR product was produced.

EXAMPLE 2

Effect of Increasing Magnesium Ion Concentration

Mg binds to PPi and therefore it is possible that the observations of Example 1 are due to chelation of Mg by excess PPi. This would lead to insufficient Mg being present to allow primer extension to proceed. In order to eliminate this possibility, the procedure of Example 1 with 3 mM PPi was repeated in the presence of various concentrations of magnesium ions.

Figure 2:
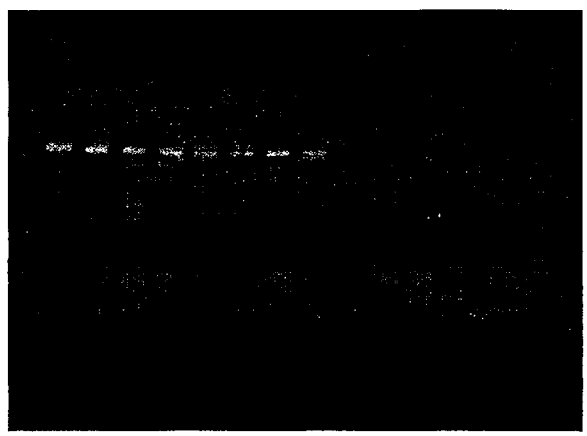
FIG. 2 shows the effect of increasing $MgCl_2$ in the absence and presence of 3 mM PPi.

The results are shown in FIG. 2. In that Figure the lanes represent the following reactions:

| Lanes | |
| --- | --- |
| 1 + 2 | 1.5 mM MgCl$_2$ |
| 3 + 4 | 5 mM MgCl$_2$ |
| 5 + 6 | 7.5 mM MgCl$_2$ |
| 7 + 8 | 10 mM MgCl$_2$ |
| 9 + 10 | 1.5 mM MgCl$_2$ + 3 mM PPi |
| 11 + 12 | 5 mM MgCl$_2$ + 3 mM PPi |
| 13 + 14 | 7.5 mM MgCl$_2$ + 3 mM PPi |
| 15 | 10 mM MgCl$_2$ + 3 mM PPi |

The results show that the addition of Mg$^{++}$ up to 10 mM final concentration (1.5 mM is standard in a PCR) does not allow PCR to occur, suggesting that it is the PPi which is blocking primer extension.

EXAMPLE 3

PCR Reactions in the Presence of Ppi and PPase

The 500 bp lambda PCR of Example 1 was repeated, but this time, 0.2 u of *Sulfolobus acidocaldarius* PPase (Sac PPase) was included in reactions containing pyrophosphate (PPi). Incubating the reaction at 95° C. for 5 mins in the presence of 0.2 u of Sac PPase was sufficient to destroy the pyrophosphate so that the PCR reaction could proceed.

Figure 3:
FIG. 3 shows the results obtained using the method of the invention and conventional PCR reaction.

The results are shown in FIG. 3 where the lanes represent the following reactions:

| Lanes | |
| --- | --- |
| | Top Row |
| 1 + 2 | 1 mM PPi + 0.2 u PPase |
| 3 + 4 | 2 mM PPi + 0.2 u Ppase |
| 5 + 6 | 3 mM PPi + 0.2 u PPase |
| 7 + 8 | 4 mM PPi + 0.2 u PPase |
| 9 + 10 | 5 mM PPi + 0.2 u PPase |
| | Bottom Row |
| 1 + 2 | 1 mM PPi |
| 3 + 4 | 2 mM PPi |
| 5 + 6 | 3 mM PPi |
| 7 + 8 | 4 mM PPi |
| 9 + 10 | 5 mM PPi |
| 11 + 12 | 0 mM PPi |

A comparable level of PCR product was generated when compared to the reaction without both PPi and PPase.

The example was repeated using concentrations of PPi of less than 1 mM. Results (not shown) indicated that 0.4 mM PPi did not completely suppress the PCR, but no PCR occurred at concentrations of 0.6 mM

EXAMPLE 4

PCR Assay

The method of the invention was then applied to an assay system that requires a "HotStart" reaction in order to generate a PCR product of the correct size.

The assay is based around the amplification of a 321 bp fragment of the human angiotensin gene. It has been recognised that the assay will only generate the correct amplification product in the presence of betaine (EP-A-0962526—see in particular Example 8).

Without betaine a HotStart DNA polymerase generates few non-specific amplification products or no products at all whereas a non-HotStart DNA polymerase PCR generates a large number of non-specific amplification products.

The PCR conditions used in the Angiotensin assay can be summarised as follows.

| Reagent | Volume | Final concn. |
|---|---|---|
| 10× Reaction Buffer | 5 μl | 1× |
| 25 mM MgCl$_2$ | 3 μl | 1.5 mM |
| 5 mM dNTPs | 2 μl | 200 μM |
| 5' primer (100 μm) | 0.25 | 0.5/μM |
| 3' primer (100 μm) | 0.25 | 0.5/μM |
| Template 100 ng/μl | 50 ng | Human xsomal DNA |
| 5 M Betaine | 10.0 | 1 M |
| DNA polymerase (5 u/μl) | 0.25 | 1.25 u |
| Water to Total volume | 50.0 μl | |

Angiotensin primer sequences

5' Primer GCA ACG CCC CTC ACT ATA AA (SEQ ID NO 16)

3' Primer GCA CCC CGC CCT TGA AGT CC (SEQ ID NO 17)

1×Reaction Buffer: 10 mM Tris. pH 8.0, 50 mM KCl. PCR conditions for the assay were as follows:
 i) 95° C. 2.00 min or less
 ii) 35 cycles of 95° C. for 15 secs
  50° C. for 30 secs
  72° C. for 30 secs
 iii) 72° C. for 7 mins
 iv) 25° C. hold The reaction was conducted using a PE9700 Instrument in the presence of 3 mM PPi and 0.2 u PPase as described in Example 3.

Figure 4:
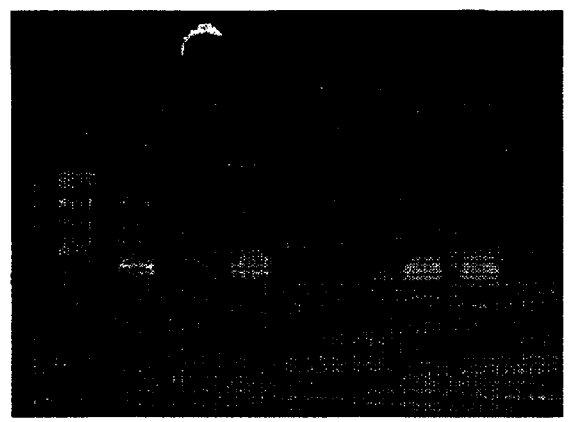
FIG. 4 shows the results obtained using the method of the invention in an assay compared to a conventional PCR assay.

The results are shown in FIG. 4 in which the Lanes shown represent the following reactions.

| Lanes | |
|---|---|
| 1 | Standard Taq polymerase PCR - without betaine - lots of false priming |
| 2 | Standard Taq polymerase PCR - with betaine - bright band is correct product - with some false priming |
| 3 | Standard Taq polymerase PCR - without betaine but plus 3 mM PPi and 0.2 u Sac PPase - No false priming at all - 5 mins denaturation at 95° C. |
| 4 | Standard Tag polymerase PCR - with betaine but plus 3 mM PPi and 0.2 u Sac PPase - only correct product - 5 mins denaturation at 95° C. |
| 5 + 6 | As per 3 but only 2 mins denaturation at 95° C. |
| 7 + 8 | As per 4 but only 2 mins denaturation at 95° C. |

It is clear that using the method of the invention, an effective "HotStart" reaction is achieved. A clear single product band was obtained using PPi and Sac PPase in the presence of betaine. In addition, no false priming was seen, even in the absence of betaine.

EXAMPLE 5
Effects of Storage at Ambient Temperature

The effect of leaving a PCR mixture containing 0.2 u Sac PPase and 3 mM PPi at room temperature 20° C. for various lengths of time prior to conducting the Angiotensin assay, was investigated. Although Sac PPase is a thermostable enzyme, it was possible that there would be a small level of enzyme activity at ambient temperatures. This might lead-to insufficient PPi in the reaction to inhibit/stop the DNA polymerase leading to primer extension and lack of "Hot-Start" functionality.

The method of Example 4 was repeated but the reaction mixtures were stored at ambient temperature for various lengths of time up to 2 hours prior to conducting the assay.

Figure 5:
FIG. 5 shows the results of an experiment to test the storage stability of PCR reaction mixtures used in the method of the invention, as compared to conventional mixtures.

The results are shown in FIG. 5 in which:
The Top Row—shows the results of a conventional Taq polymerase PCR of angiotensin (with and without betaine present) following incubation of reagents at room temperature for the time shown; and
The Bottom Row shows the results of a similar set of assays in accordance with the method of the invention where, in all cases, the assay mix contained 3 mM PPi and 0.2 u PPase per 50 ul PCR.

| Lanes | Presence of betaine | Time at 22° C. (Room Temp) |
|---|---|---|
| 1 + 2 | − | 0 |
| 3 + 4 | + | 0 |
| 5 + 6 | − | 30 mins |
| 7 + 8 | + | 30 mins |
| 9 + 10 | − | 60 mins |
| 11 + 12 | + | 60 mins |
| 13 + 14 | − | 120 mins |
| 15 + 16 | + | 120 mins |

Even after two hours, assay conducted in accordance with the present invention functioned as expected, suggesting there is insufficient ambient temperature digestion of the PPi by the Sac PPase.

The result shown in FIG. 5 showed that a 2 hour incubation of the PCR mix at room temperature, prior to PCR, had no effect on the specificity providing PPi and Sac PPase was used.

Figure 6:
FIG. 6 shows the results of the use of a different PPase in the method of the invention.

EXAMPLE 6
Use of Other Thermostable PPase Enzymes in the Method of the Invention The assay described in Example 4 was repeated alongside a similar reaction using a different commercially available thermostable PPase (with different unit definition of activity) in place of Sac PPase. The results are shown in FIG. 6 in which the lanes represent the following reactions:

| Lanes | |
|---|---|
| 1 + 2 | Standard Taq polymerase PCR - without betaine |
| 3 + 4 | Standard Taq polymerase PCR - with betaine |
| 5 + 6 | Standard Taq polymerase PCR - without betaine but plus 3 mM PPi and 0.2 u Sac PPase |
| 7 + 8 | Standard Taq polymerase PCR - with betaine plus 3 mM PPi and 0.2 u Sac PPase |
| 9 + 10 | Standard Taq polymerase PCR - without betaine but plus 3 mM PPi and 10 u* *Thermococcus litoralis* PPase |
| 11 + 12 | Standard Taq polymerase PCR - with betaine plus 3 mM PPi and 10 u* *Thermococcus litoralis* PPase |

*Units used in this case were as supplied by the manufacturer and are defined as the amount of enzyme that will generate 40 nmoles of phosphate per minute under standard reaction conditions (10 minute reaction at 75° C. in 50 mM Tricine [pH 8.5], 1 mM MgCl$_2$, 0.32 mM PPi, reaction volume of 0.5 ml).

*Thermococcus litoralis* PPase (available from New England Biolabs) appears to have the same effect as Sac PPase in this assay.

EXAMPLE 7
Use of Different Thermostable DNA Polymerases in the Method of the Invention A variety of thermostable DNA polymerases were employed in the method of the invention and some comparative assays. These included several non-proofreading *Thermus* sp. DNA polymerases, proof-reading hyperthermophilic archael DNA polymerases and mixes of non-proofreading and proofreading DNA polymerases.

Figure 7A:
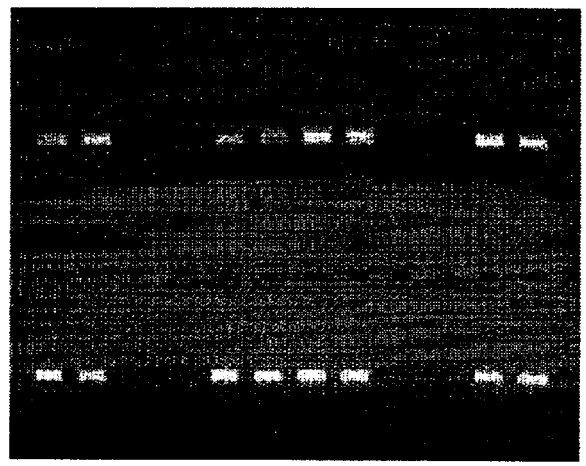
FIGS. 7a and 7b and FIGS. 8a and 8b show the results of PCR experiments using the method of the invention and a variety of different DNA polymerases.
Figure 7B:
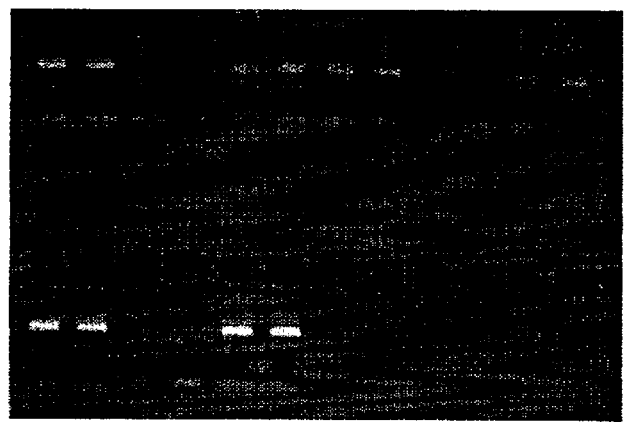
Figure 8A:
Figure 8B:

They were all tested using the 500 bp lambda PCR as described in Example 1 (FIGS. 7a and 7b), and several using the Angiotensin assay as described in Example 4 (FIGS. 8a and 8b).

Details of the assay conditions are summarised as follows:

FIG. 7a—Thermus DNA polymerases

| Lanes | |
|---|---|
| | Top Row |
| 1 + 2 | Taq polymerase 0 mM PPi and no PPase |
| 3 + 4 | Taq polymerase 3 mM PPi and no PPase |
| 5 + 6 | Taq polymerase 3 mM PPi and 0.2 u Sac PPase |
| 7 + 8 | Tbr polymerase 0 mM PPi and no PPase |
| 9 + 10 | Tbr polymerase 3 mM PPi and no PPase |
| 11 + 12 | Tbr polymerase 3 mM PPi and 0.2 u Sac PPase |
| | Bottom Row |
| 1 + 2 | Tth polymerase 0 mM PPi and no PPase |
| 3 + 4 | Tth polymerase 3 mM PPi and no PPase |
| 5 + 6 | Tth polymerase 3 mM PPi and 0.2 u Sac PPase |
| 7 + 8 | TspNH polymerase 0 mM PPi and no PPase |
| 9 + 10 | TspNH polymerase 3 mM PPi and no PPase |
| 11 + 12 | TspNH polymerase 3 mM PPi and 0.2 u Sac PPase |

FIG. 7b—Archael Proof-reading DNA polymerases

| Lanes | |
|---|---|
| | Top Row |
| 1 + 2 | Pfu polymerase 0 mM PPi and no PPase |
| 3 + 4 | Pfu polymerase 3 mM PPi and no PPase |
| 5 + 6 | Pfu polymerase 3 mM PPi and 0.2 u Sac PPase |
| 7 + 8 | 9° N exo- polymerase 0 mM PPi and no PPase |
| 9 + 10 | 9° N exo- polymerase 3 mM PPi and no PPase |
| 11 + 12 | 9° N exo- polymerase 3 mM PPi and 0.2 u Sac PPase |
| | Bottom Row |
| 1 + 2 | VENT polymerase 0 mM PPi and no PPase |
| 3 + 4 | VENT polymerase 3 mM PPi and no PPase |
| 5 + 6 | VENT polymerase 3 mM PPi and 0.2 u Sac PPase |

FIG. 8a Angiotensin assay without PPi and without Sac PPase (with and without Betaine)

| Lanes | |
|---|---|
| 1 + 2 | Taq polymerase without betaine |
| 3 + 4 | Taq polymerase with betaine |
| 5 + 6 | Accurase polymerase without betaine |
| 7 + 8 | Accurase polymerase with betaine |
| 9 + 10 | Tbr polymerase without betaine |
| 11 + 12 | Tbr polymerase with betaine |
| 13 + 14 | Tth polymerase without betaine |
| 15 + 16 | Tth polymerase with betaine |

FIG. 8b Angiotensin assay with PPi and Sac PPase (with and without Betaine)

Control Lanes 1–4 (Top Row) and 12–16 (Bottom Row)

| Lanes | |
|---|---|
| | Top Row |
| 1 + 2 | Taq polymerase without betaine but plus 3 mM PPi - No Sac PPase |
| 3 + 4 | Taq polymerase with betaine but plus 3 mM PPi - - No Sac PPase |
| | All below with 3 mM PPi and 0.2 u Sac PPase |
| 5 + 6 | Taq polymerase without betaine |
| 7 + 8 | Taq polymerase with betaine |
| 9 + 10 | Accurase polymerase without betaine |
| 11 + 12 | Accurase polymerase with betaine |
| 13 + 14 | Tbr polymerase without betaine |
| 15 + 16 | Tbr polymerase with betaine |
| | Bottom Row |
| | All below with 3 mM PPi and 0.2 u Sac PPase |
| 1 + 2 | Tth polymerase without betaine |
| 3 + 4 | Tth polymerase with betaine |
| 5 + 6 | TspNH polymerase without betaine |
| 7 + 8 | TspNH polymerase with betaine |
| 9 + 10 | Pfu polymerase without betaine |
| 11 + 12 | Pfu polymerase with betaine |
| 13 + 14 | Taq polymerase control without betaine and no PPi or PPase |
| 15 + 16 | Taq polymerase control with betaine and no PPi or PPase |

All DNA polymerases tested were inhibited by PPi and that inhibition could be overcome with Sac PPase.

COMPARATIVE EXAMPLE 8

Comparison of Method of Invention with Conventional "Hotstart" Methodologies

We have some initial results (FIGS. 9 and 10) that show that a chemically modified Taq polymerase (modified as described in U.S. Pat. No. 5,677,152) does generate some false PCR products in the absence of betaine but gives the correct product in the presence of betaine.

Figure 9:
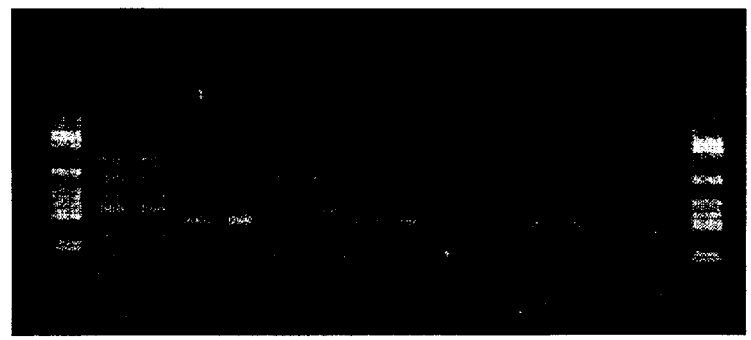
FIG. 9 shows the results of an experiment comparing a conventional "Hot Start" PCR with the method of the invention.

FIG. 9 Angiotensin assay

| Lanes | |
|---|---|
| 1 + 2 | Taq polymerase without betaine |
| 3 + 4 | Taq polymerase with betaine |
| 5 + 6 | Chemically modified Taq without betaine |
| 7 + 8 | Chemically modified Taq with betaine |
| 9 + 10 | Method of the invention (3 mM PPi and 2 u Sac PPase) without betiane |
| 11 + 12 | Method of the invention (3 mM PPi and 2 u Sac PPase) with betaine |

It appears that under these circumstances, the chemically modified enzyme is inactive until it has a 10 min activation at 95° C. Without this preliminary incubation, negligible PCR product was generated. The apparent false priming and generation of wrong PCR products in the absence of betaine is difficult to explain however, since the chemically modified Taq is inactive at room temperature.

Figure 10:
FIG. 10 shows the results obtained by carrying out a similar assay but using an alternative conventional PCR.
Figure 17:
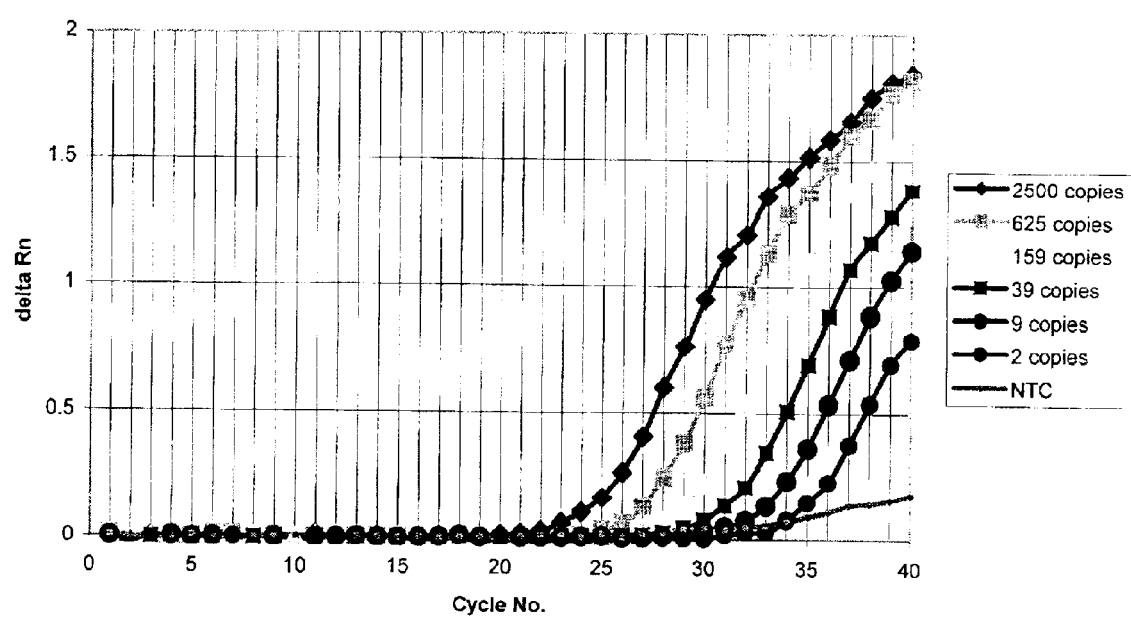
FIG. 17 shows the results of the method of the invention using the inorganic pyrophosphatase from *Aeropyrum pernix*.

FIG. 10 Angiotensin assay with Taq and anti-Taq antibody

| Lanes | |
|---|---|
| 1 + 2 | Anti-Taq antibody plus Taq polymerase without betaine |
| 3 + 4 | Anti-Taq antibody plus Taq polymerase with betaine |

In an anti-Taq DNA polymerase antibody mediated HotStart, a substantial number of false products are generated in the absence of betaine (similar to a standard Taq polymerase PCR without betaine) and a minor false product is also generated along with the correct product in the presence of betaine.

The method of the invention appears to give a rapid PCR reaction which is more specific than both of these commercial HotStart methodologies.

EXAMPLE 9

Isolation of Inorganic Pyrophosphatase from *Aeropyrum pernix*

*Aeropyrum pernix* was obtained from the J.C.M. culture collection. The inorganic pyrophosphatase enzyme was cloned, expressed and purified.

Cloning and Expression of Inorganic Pyrophosphatase from *A.pernix*

The genome sequence comprising the pyrophosphatase gene of *Aeropyrum pernix* is shown in FIG. 11. The primers used were designed from the genome sequence of Aeropyrum pernix. These are shown below as 5' to 3' with the restriction sites shown in bold.

```
Upper primer, introducing the Nde I site:
TGCATGCATATGACAGGCTGTCTGAAATTG          (SEQ ID NO 18)

Lower primer, introducing the Hind III site:
TAAGTGTAAGCTTGACTGTGGGGCGGTGAAAG        (SEQ ID NO 19)
```

Aligning the putative sequence from the genome with other pyrophosphates genes suggested that a later ATG should be the start methionine and not the one shown in the databank (shown in italics in SEQ ID NO.1 in FIG. 11) and that the amino acid sequence of the enzyme is, in fact, as shown in SEQ ID NO 25. Primers were therefore designed corresponding to the later methionine (shown in bold in SEQ ID NO.1 in FIG. 11).

A PCR was run using 100 ng of the *Aeropyrum pernix* DNA in a 100 µl volume with 50 pM of the above primers. 20 cycles were run with 55° C. annealing and a 45 second extension time.

Initial hold of 3 mins at 94° C.
20 Cycles of 94° C., 10 secs, 55° C., 10 secs, 68° C., 45 secs.
Final hold of 72° C. 7 minutes
PCR Conditions.
50 pM Upper Primer (5' . . . TGCATGCATATGACAGGCTGTCTGAAAATTG . . . 3'-SEQ ID NO 20)
50 pM Lower Primer (5' . . . TAAGTGTAAGCTTGACTGTGGGGGCGGTGAAAG . . . 3'-SEQ ID NO 21)
1.5 mM MgCl$_2$
1.25 u Accurase DNA polymerase (Cat. No. AC001, GeneSys Ltd.)
75 mM Tris, pH 8.8
20 mM Ammonium sulphate
0.1% (w/v) Tween20
100 ng *Aeropyrum pernix* genomic DNA The PCR product was 686 base pairs long as shown in FIG. 13. The PCR product was Prepanol™ (Cat. No. P001, GeneSys Ltd.) precipitated following the manufacturers recommended conditions and finally re-suspended in 10 mM Tris, 0.1 mM EDTA.

The PCR product was digested with restriction enzymes Nde I and Hind III, phenol extracted, precipitated with ethanol and re-suspended in 10 mM Tris, 0.1 mM EDTA.

pTTQ18NHK vector (shown in FIG. 15) had also been digested with Nde I and Hind III, phenol extracted, ethanol precipitated and re-suspended in 10 mM Tris, 0.1 mM EDTA.

100 ng cut PCR sequence was ligated with 1 µg of cut pTTQ18NHK vector (see FIG. 16) in a total volume of 10 µl, overnight at 16° C. in 1x NEB ligation buffer using 200 u of New England Biolabs T4 DNA ligase. The plasmid vector was pTTQ18NHK, a modified form of vector pTTQ18 (Stark M J, Gene, 1987; 51(2–3):255–67) containing a kanamycin antibiotic gene inserted at the unique Eco0109 I restriction enzyme site and a replacement polylinker (see FIG. 14) inserted between the EcoR I site and Hind III site of the original vector.

20 µl of water was added and the reaction heated to 70° C. for 20 mins. 1/10 volume of 3M sodium acetate, pH 5.2 and 2 volumes of ethanol added. It was mixed and stored at –20° C. for 1 hour. After microfuging at 10,000 g for 10 mins, the supernatant was removed from the pelleted DNA and the DNA re-suspended in 5 µl water.

0.5 µl was electroporated into *E.coli* TOP10F' cells and following 1 hour recovery at 37° C., aliquots of the cells were plated on Kanamycin Luria Broth agar plates. The plates were incubated at 37° C. overnight.

Colonies were gridded in duplicate on both a fresh Kanamycin Luria Broth agar plate and a Kanamycin Luria Broth agar plate prepared by addition of 1 µl of 20 mg/ml XGAL and 1 µl of 0.5M IPTG per ml of agar gel (KIX plate).

Following overnight incubation at 37° C., white colonies on the KIX plate were screened by PCR with M13 forward and reverse primers for the presence of an insert corresponding to the *Aeropyrum pernix* PCR product.

9 colonies containing a 701 bp product were grown up in 20 ml LB plus 100 µg/ml Kanamycin to an OD600 of 1.0 then expression was induced by addition of IPTG to 0.5 mM final. Cells were grown for a further 4 hours and then the cells harvested and stored frozen at –20° C.

Cells were lysed by addition of 0.5 ml 50 mM Tris-HCl, pH 7.9, 50 mM dextrose, 1 mM EDTA and 0.5 ml 10 mM Tris-HCl, pH 7.9, 50 mM KCl, 1 mM EDTA, 0.5% v/v) Tween 20, 0.5% (v/v) Nonidet-P40 and incubation at 80° C. for 15 minutes.

Following centrifugation at 10,000 g for 10 minutes at room temperature, an aliquot from each lysed cells were analysed by SDS polyacrylamide gel electrophoresis using a 12% gel. The gel was run then stained with Coomassie blue R250. All samples showed a band of approx 23 kDa, which corresponds to the size of the putative PPase.

The same samples were then assayed for PPase activity at 75° C. using the colorimetric assay of Jukka K. Heinonen, Reijo J. Lahti. (1981) Analytical Biochemistry, Vol.113, pp313–317.

All samples showed as positive, confirming that the expressed protein possessed thermophilic inorganic pyrophosphatase activity.

The first clone was subsequently used for larger scale production of the protein.

Purification of the Pyrophosphatase

This clone was in 24 liters of LB. Once the OD$_{600}$ reached approximately 1.5, the culture was induced with 0.5 mM IPTG and left to grow for a further 4 hours. The cells were then harvested and the cell pellet lysed. The expressed enzyme was purified by standard column chromatography on phenyl-sepharose CL4B (Amersham Pharmacia Biotech), hydroxylapatite (Bio-rad Laboratories) and Hi-Performance Q Sepharose (Amersham Pharmacia Biotech), finally being stored at –20° C. in 20 mM Tris-HCl, pH 8.0, 100 mM NaCl, 0.5% (v/v) Tween 20, 0.5% (v/v) Nonidet P40, 0.1 mM EDTA, 1 mM dithiothreitol and 50% glycerol.

EXAMPLE 10

PCR Assay using the *A. pernix* Inorganic Pyrophosphatase Enzyme

The method of the present invention was carried out using the *A. pernix* inorganic pyrophosphatase enzyme. The assay is based around the amplification of the human B-actin gene.

In this assay, a kit was used which was obtained from from Eurogentec S. A., Parc Scientifique du Sart-Tilman, rue Bois Saint-Jean 14, 4102 SERAING, Belgium (Cat. No. RT-QP73-05). The standard Taq polymerase was substituted for the HotStart Taq polymerase provided with the kit.

PCR Reaction Mixture
1×Reaction Buffer
200 µM, DATP, dCTP, dGTP and 400 µM dUTP
0.025 u/µl unmodified Taq polymerase
0.002 u/µl *Aeropyrum pernix* inorganic pyrophosphatase
0.3 µM 5' Primer (5' GAC TCG TCA TAC TCC TGC TTG CT 3'—SEQ ID NO 22)
0.3 µM 3' Primer (5' CAT TGC CGA CAG GAT GCA GAA 3'—SEQ ID NO 23)
0.15 µM Taqman probe (FAM-ATCCACATCTGCTGGAAGGTGGACAGT-TAMRA—SEQ ID NO 24)
5 mM MgCl$_2$
2 mM NaPPi Passive Reference
1 in 4 dilutions of Human genomic DNA starting with 7.5 ng (2500 copies)

Cycling Conditions
Initial denaturation of 94° C. 3 minutes
40 cycles of 94° C., 15 seconds and 60° C., 60 seconds
The results are shown in FIG. 19.

In conclusion we believe that using the method of the invention, by using pyrophosphate to inhibit a PCR and then removing that inhibition, for example at 80° C.–95° C. through the use of a thermostable PPase, behaves in the same manner as HotStart PCR but at a rapid rate with the additional benefit of increased specificity.

All references mentioned in the above specification are herein incorporated by reference. Other modifications of the present invention will be apparent to those skilled in the art without departing from the scope and spirit of the invention. Although the invention has been described in connection with the specific preferred embodiments, it should be understood that the invention as claimed should not be unduly limited to such specific embodiments. Indeed, various modifications of the described modes for carrying out the invention, which are obvious to those skilled in the art, are intended to be within the scope of the following claims.

---

What is claimed is:

1. A method for conducting a nucleic acid amplification reaction, the method comprising forming a polymerase chain reaction (PCR) reaction mixture by mixing together reagents necessary for carrying out an amplification reaction and a sufficient amount of a pyrophosphate salt to prevent primer extension, adding to the mixture at least 0.04 units of a thermostable pyrophosphatase enzyme (PPase) per 50 µL PCR reaction mixture, and subjecting the reaction mixture to conditions such that the pyrophosphate salt is digested with a pyrophosphatase enzyme (PPase) whereupon an amplification reaction is carried out.

2. The method of claim 1 wherein the reaction mixture contains a DNA polymerase which is selected from the group consisting of *Thermus aquaticus* polymerase (Taq), *Thermus thermophilus* polymerase (Tth), *Thermus* species NH polymerase (TspNH), *Thermus brockianus* polymerase (Thr), *Pyrococcus furiosus* polymerase (Pfu), 9°N7 exo- DNa polymerase, and *Thermococcus literalis* DNA polymerase.

3. The method of claim 1 wherein the pyrophosphate is an alkali earth metal pyrophosphate.

4. The method of claim 3 wherein the pyrophosphate is a tetrasodium pyrophosphate of formula $Na_4P_2O_7$.

5. The method of claim 1 wherein the pyrophosphate is present in the reaction mixture at a concentration of at least 0.5 mM.

6. The method of claim 1 wherein the pyrophosphate is present at a concentration of from 1–10 mM.

7. The method of claim 1 wherein the thermostable PPase is *Sulfolbus acidicaldarius* inorganic pyrophosphatase, (Sac PPase), *Thermococcus litoralis* inorganic pyrophosphatase or *Aeropyrum pernix* inorganic pyrophosphatase.

8. The method of claim 1 wherein the thermostable PPase is added to the reaction mixture on formation thereof.

9. The method of claim 8 further comprising an incubation step prior to the amplification reaction, wherein the reaction mixture is incubated at elevated temperature and the PPase digests the inorganic pyrophosphate present.

10. The method of claim 1 wherein the concentration of PPase is at least 0.08 units per 50 µL reaction mixture.

11. The method of claim 1 wherein the concentration of PPase is from about 0.2–10 units per 50 µL reaction mixture.

12. An isolated pyrophosphatase enzyme encoded by the polynucleotide sequence as shown in SEQ ID NO:26 or a fragment thereof having pyrophosphatase enzymatic activity.

13. An isolated pyrophosphatase enzyme having the amino acid sequence as shown in SEQ ID NO:25 or a fragment thereof having pyrophosphatase enzymatic activity.

14. An isolated polynucleotide which encodes a pyrophosphatase enzyme, wherein the pyrophosphatase enzyme has the amino acid sequence of SEQ ID NO:25, or a fragment thereof having pyrophosphatase enzymatic activity.

15. A method for conducting a nucleic acid amplification reaction comprising
   forming a PCR reaction mixture by mixing together reagents necessary for carrying out a PCR amplification reaction and a sufficient amount of a pyrophosphate salt to prevent primer extension,
   adding to the mixture a thermostable pyrophosphatase enzyme (PPase) which is obtainable from a hyperthermophilic archeaon and wherein the concentration of PPase in the reaction mixture is at least 0.04 u per 50 µL PCR reaction mixture, and
   subjecting the reaction mixture to conditions such that the pyrophosphate salt is digested with pyrophosphatase enzyme (PPase), whereupon an amplification reaction is carried out.

16. The method of claim 15 wherein the reaction mixture contains a DNA polymerase selected from the group consisting of *Thermus aquaticus* polymerase (Taq), *Thermus thermophilus* polymerase (Tth), *Thermus* species NH polymerase (TspNH), *Thermus brockianus* polymerase (Tbr), *Pyrococcus furiosus* polymerase (Pfu), 9°N7 exo-DNa polymerase, and *Thermococcus literalis* DNA polymerase.

17. The method of claim 15 wherein the pyrophosphate is an alkali earth metal pyrophosphate.

18. The method of claim 17 wherein the pyrophosphate is a tetrasodium pyrophosphate of formula $Na_4P_2O_7$.

19. The method of claim 15 wherein the pyrophosphate is present in the reaction mixture at a concentration of at least 0.5 mM.

20. The method of claim 15 wherein the pyrophosphate is present at a concentration of from 1–10 mM.

21. The method of claim 15 wherein the thermostable PPase is *Sulfolbus acidicaldarius* inorganic pyrophosphatase, (Sac PPase), *Thermococcus litoralis* inorganic pyrophosphatase or *Aeropyrum pernix* inorganic pyrophosphatase.

22. The method of claim 15 wherein the thermostable PPase is added to the reaction mixture on formation thereof.

23. The method of claim 15 further comprising an incubation step prior to the amplification reaction, wherein the reaction mixture is incubated at elevated temperature and the PPase digests the pyrophosphate present.

24. The method ot claim 15 wherein the concentration of PPase is at least 0.08 units per 50 µL reaction mixture.

25. The method of claim 15 wherein the concentration of PPase is from about 0.2–10 units per 50 µL PCR reaction mixture.

* * * * *

SEQUENCE LISTING

```
<160> NUMBER OF SEQ ID NOS: 26

<210> SEQ ID NO 1
<211> LENGTH: 960
<212> TYPE: DNA
<213> ORGANISM: Aeropyrum pernix

<400> SEQUENCE: 1
taatcctaat tcgctttatg tggacgatcc ttcccagcaa aaccgggttt gttaacagcc      60
ttagctttat aactcgacta gccaaactat cggttagacg ggtgcatgca atgacaggct     120
gtctgaaaat tggtcctgga gatgaggctc cagatgttgt gaatgtcgtt atagagatac     180
ctatgaacag ttctgttaag tacgagttcg acaaggaggc gtgtattgtt aaggttgata     240
ggttccttta caccagcatg gtctacccct tcaactacgg gttcatacca ggcactctag     300
aggaggacgg agatcctgtt gacgttctag ttattagccg ggagcccgtt gctcccggct     360
cgcttataga ggctgtgccc gtggccgtgt tagacatgga ggacgaggag ggtccggaca     420
gcaaggttgt tgccgtaccc aaggccaagc tggaccccct attcgccagc tataaggacg     480
ttggcgacat acctgatgcc ctgaaatcca agataaagca cttcttcgag cactataagg     540
agctggagcc tggaaagtgg gttagagtga ctggatggag gcctgctgcc gatgcgaagg     600
agattataag gagggctata gagaggtata aggggcgtg atgagggctt aacggctcac      660
gttttctggg agagtgtcgc acctttgagg gcgatcaccc tcgccagcgt gcgtgtgctt     720
ttgtctatga ttatggctac agttcttcta gccgctttca ccgcccccac agtcaataca     780
cttacaccta gaggttctgc gctgtatgct gtggatgtag ttgtagtaga cgccagcaca     840
ggatctgccc tggggttctc ccggtttgtc gtatccgcct acagaggggg ggtcggggat     900
gtgggtgtta tctactcttc gggggtctca gtatcagggt ctagtctgga aaggctgctg     960

<210> SEQ ID NO 2
<211> LENGTH: 207
```

```
<212> TYPE: PRT
<213> ORGANISM: Aeropyrum pernix

<400> SEQUENCE: 2

Met Trp Thr Ile Leu Pro Ser Lys Thr Gly Phe Val Asn Ser Leu Ser
  1               5                  10                  15

Phe Ile Thr Arg Leu Ala Lys Leu Ser Val Arg Arg Val His Ala Met
             20                  25                  30

Thr Gly Cys Leu Lys Ile Gly Pro Gly Asp Glu Ala Pro Asp Val Val
         35                  40                  45

Asn Val Val Ile Glu Ile Pro Met Asn Ser Ser Val Lys Tyr Glu Phe
     50                  55                  60

Asp Lys Glu Ala Cys Ile Val Lys Val Asp Arg Phe Leu Tyr Thr Ser
 65                  70                  75                  80

Met Val Tyr Pro Phe Asn Tyr Gly Phe Ile Pro Gly Thr Leu Glu Glu
                 85                  90                  95

Asp Gly Asp Pro Val Asp Val Leu Val Ile Ser Arg Glu Pro Val Ala
            100                 105                 110

Pro Gly Ser Leu Ile Glu Ala Val Pro Val Ala Val Leu Asp Met Glu
        115                 120                 125

Asp Glu Glu Gly Pro Asp Ser Lys Val Val Ala Val Pro Lys Ala Lys
130                 135                 140

Leu Asp Pro Leu Phe Ala Ser Tyr Lys Asp Val Gly Asp Ile Pro Asp
145                 150                 155                 160

Ala Leu Lys Ser Lys Ile Lys His Phe Phe Glu His Tyr Lys Glu Leu
                165                 170                 175

Glu Pro Gly Lys Trp Val Arg Val Thr Gly Trp Arg Pro Ala Ala Asp
            180                 185                 190

Ala Lys Glu Ile Ile Arg Arg Ala Ile Glu Arg Tyr Lys Gly Ala
        195                 200                 205

<210> SEQ ID NO 3
<211> LENGTH: 173
<212> TYPE: PRT
<213> ORGANISM: Sulfolobus solfataricus

<400> SEQUENCE: 3

Met Lys Leu Ser Pro Gly Lys Asn Ala Pro Asp Val Val Asn Val Leu
  1               5                  10                  15

Val Glu Ile Pro Gln Gly Ser Asn Ile Lys Tyr Glu Tyr Asp Asp Glu
             20                  25                  30

Glu Gly Val Ile Lys Val Asp Arg Val Leu Tyr Thr Ser Met Asn Tyr
         35                  40                  45

Pro Phe Asn Tyr Gly Phe Ile Pro Gly Thr Leu Glu Glu Asp Gly Asp
     50                  55                  60

Pro Leu Asp Val Leu Val Ile Thr Asn Tyr Gln Leu Tyr Pro Gly Ser
 65                  70                  75                  80

Val Ile Glu Val Arg Pro Ile Gly Ile Leu Tyr Met Lys Asp Glu Glu
                 85                  90                  95

Gly Glu Asp Ala Lys Ile Val Ala Val Pro Lys Asp Lys Thr Asp Pro
            100                 105                 110

Ser Phe Ser Asn Ile Lys Asp Ile Asn Asp Leu Pro Gln Ala Thr Lys
        115                 120                 125

Asn Lys Ile Val His Phe Phe Glu His Tyr Lys Glu Leu Glu Pro Gly
130                 135                 140
```

```
Lys Tyr Val Lys Ile Ser Gly Trp Gly Ser Ala Thr Glu Ala Lys Asn
145                 150                 155                 160

Arg Ile Gln Leu Ala Ile Lys Arg Val Ser Gly Gly Gln
                165                 170

<210> SEQ ID NO 4
<211> LENGTH: 176
<212> TYPE: PRT
<213> ORGANISM: Escherichia coli

<400> SEQUENCE: 4

Met Ser Leu Leu Asn Gly Pro Ala Gly Lys Asp Leu Pro Glu Asp Ile
1               5                   10                  15

Tyr Val Val Ile Glu Ile Pro Ala Asn Ala Asp Pro Ile Lys Tyr Glu
                20                  25                  30

Ile Asp Lys Glu Ser Gly Ala Leu Phe Val Asp Arg Phe Met Ser Thr
            35                  40                  45

Ala Met Phe Tyr Pro Cys Asn Tyr Gly Tyr Ile Asn His Ile Leu Ser
        50                  55                  60

Leu Asp Gly Asp Pro Val Asp Val Leu Val Pro Thr Pro Tyr Pro Leu
65                  70                  75                  80

Gln Pro Gly Ser Val Ile Arg Cys Arg Pro Val Gly Val Leu Lys Met
                85                  90                  95

Thr Asp Glu Ala Gly Glu Asp Ala Lys Leu Val Ala Val Pro His Ser
            100                 105                 110

Lys Leu Ser Lys Glu Tyr Asp His Ile Lys Asp Val Asn Asp Leu Pro
        115                 120                 125

Glu Leu Leu Lys Ala Gln Ile Ala His Phe Phe Glu His Tyr Lys Asp
    130                 135                 140

Leu Glu Lys Gly Lys Trp Val Lys Val Glu Gly Trp Glu Asn Ala Glu
145                 150                 155                 160

Ala Ala Lys Ala Glu Ile Val Ala Ser Phe Glu Arg Ala Lys Asn Lys
                165                 170                 175

<210> SEQ ID NO 5
<211> LENGTH: 178
<212> TYPE: PRT
<213> ORGANISM: Aquifex aeolicus

<400> SEQUENCE: 5

Met Gly Tyr Asp Gln Leu Pro Pro Gly Lys Asn Pro Pro Glu Asp Ile
1               5                   10                  15

Tyr Val Val Ile Glu Ile Pro Gln Gly Ser Ala Val Lys Tyr Glu Leu
                20                  25                  30

Asp Lys Asp Thr Gly Val Ile Phe Val Asp Arg Phe Leu Phe Thr Ala
            35                  40                  45

Met Tyr Tyr Pro Phe Asn Tyr Gly Phe Val Pro Gln Thr Leu Ala Asp
        50                  55                  60

Asp Gly Asp Pro Val Asp Val Leu Val Ile Ser Arg Glu Pro Val Val
65                  70                  75                  80

Pro Gly Ala Val Met Arg Cys Arg Pro Ile Gly Met Leu Glu Met Arg
                85                  90                  95

Asp Glu Ala Gly Ile Asp Thr Lys Val Ile Ala Val Pro His Glu Lys
            100                 105                 110

Leu Asp Pro Ser Tyr Ser Asn Ile Lys Thr Val Asp Asn Leu Pro Glu
        115                 120                 125
```

```
Ile Val Arg Glu Lys Ile Lys His Phe Phe Glu His Tyr Lys Glu Leu
        130                 135                 140

Glu Pro Gly Lys Trp Val Lys Val Glu Asn Trp Lys Gly Leu Gln Asp
145                 150                 155                 160

Ala Ile Glu Glu Ile Lys Lys Gly Ile Glu Asn Tyr Lys Asn Lys
                165                 170                 175

Glu Gly

<210> SEQ ID NO 6
<211> LENGTH: 178
<212> TYPE: PRT
<213> ORGANISM: Pyrococcus horikoshii

<400> SEQUENCE: 6

Met Asn Pro Phe His Asp Leu Glu Pro Gly Pro Asn Val Pro Glu Val
  1               5                  10                  15

Val Tyr Ala Leu Ile Glu Ile Pro Lys Gly Ser Arg Asn Lys Tyr Glu
             20                  25                  30

Leu Asp Lys Glu Thr Gly Leu Leu Lys Leu Asp Arg Val Leu Tyr Thr
         35                  40                  45

Pro Phe His Tyr Pro Val Asp Tyr Gly Ile Ile Pro Arg Thr Trp Tyr
 50                  55                  60

Glu Asp Gly Asp Pro Phe Asp Ile Met Val Ile Met Arg Glu Pro Thr
65                  70                  75                  80

Tyr Pro Leu Thr Ile Ile Glu Ala Arg Pro Ile Gly Leu Phe Lys Met
                 85                  90                  95

Ile Asp Ser Gly Asp Lys Asp Tyr Lys Val Leu Ala Val Pro Val Glu
                100                 105                 110

Asp Pro Tyr Phe Lys Asp Trp Lys Asp Ile Ser Asp Val Pro Lys Ala
            115                 120                 125

Phe Leu Asp Glu Ile Ala His Phe Phe Lys Arg Tyr Lys Glu Leu Glu
        130                 135                 140

Gly Lys Glu Ile Ile Val Glu Gly Trp Glu Gly Ala Glu Ala Ala Lys
145                 150                 155                 160

Arg Glu Ile Leu Arg Ala Ile Glu Met Tyr Lys Glu Lys Phe Gly Lys
                165                 170                 175

Lys Glu

<210> SEQ ID NO 7
<211> LENGTH: 178
<212> TYPE: PRT
<213> ORGANISM: Pyrococcus abyssi

<400> SEQUENCE: 7

Met Asn Pro Phe His Asp Leu Glu Pro Gly Pro Asn Val Pro Glu Val
  1               5                  10                  15

Val Tyr Ala Leu Ile Glu Ile Pro Lys Gly Ser Arg Asn Lys Tyr Glu
             20                  25                  30

Leu Asp Lys Lys Thr Gly Leu Leu Lys Leu Asp Arg Val Leu Tyr Ser
         35                  40                  45

Pro Phe Phe Tyr Pro Val Asp Tyr Gly Ile Ile Pro Arg Thr Trp Tyr
 50                  55                  60

Asp Asp Asp Asp Pro Phe Asp Ile Met Val Ile Met Arg Glu Pro Thr
65                  70                  75                  80

Tyr Pro Leu Thr Ile Ile Glu Ala Arg Pro Ile Gly Leu Phe Lys Met
                 85                  90                  95
```

```
Ile Asp Ser Gly Asp Lys Asp Tyr Lys Val Leu Ala Val Pro Val Glu
            100                 105                 110

Asp Pro Tyr Phe Lys Asp Trp Lys Asp Ile Asp Val Pro Lys Ala
            115                 120                 125

Phe Leu Asp Glu Ile Ala His Phe Lys Arg Tyr Lys Glu Leu Gln
            130                 135                 140

Gly Lys Glu Ile Ile Val Glu Gly Trp Glu Ala Glu Ala Lys
145                 150                 155                 160

Arg Glu Ile Leu Arg Ala Ile Glu Leu Tyr Lys Glu Lys Phe Gly Ser
                165                 170                 175

Lys Glu

<210> SEQ ID NO 8
<211> LENGTH: 176
<212> TYPE: PRT
<213> ORGANISM: Thermococcus litoralis

<400> SEQUENCE: 8

Met Asn Pro Phe His Asp Leu Glu Pro Gly Pro Glu Val Pro Glu Val
 1               5                  10                  15

Val Tyr Ala Leu Ile Glu Ile Pro Lys Gly Ser Arg Asn Lys Tyr Glu
                20                  25                  30

Leu Asp Lys Lys Thr Gly Leu Ile Lys Leu Asp Arg Val Leu Tyr Ser
            35                  40                  45

Pro Phe His Tyr Pro Val Asp Tyr Gly Ile Ile Pro Gln Thr Trp Tyr
        50                  55                  60

Asp Asp Asp Asp Pro Phe Asp Ile Met Val Ile Met Arg Glu Pro Thr
65                  70                  75                  80

Tyr Pro Gly Val Leu Ile Glu Ala Arg Pro Ile Gly Leu Phe Lys Met
                85                  90                  95

Ile Asp Ser Gly Asp Lys Asp Tyr Lys Val Leu Ala Val Pro Val Glu
            100                 105                 110

Asp Pro Tyr Phe Asn Asp Trp Lys Asp Ile Ser Asp Val Pro Lys Ala
            115                 120                 125

Phe Leu Asp Glu Ile Ala His Phe Phe Gln Arg Tyr Lys Glu Leu Gln
            130                 135                 140

Gly Lys Glu Ile Ile Val Glu Gly Trp Glu Asn Ala Glu Lys Ala Lys
145                 150                 155                 160

Gln Glu Ile Leu Arg Ala Ile Glu Leu Tyr Lys Glu Lys Phe Lys Lys
                165                 170                 175

<210> SEQ ID NO 9
<211> LENGTH: 179
<212> TYPE: PRT
<213> ORGANISM: Thermoplasma acidophilum

<400> SEQUENCE: 9

Met Glu Ser Phe Tyr His Ser Val Pro Val Gly Pro Lys Pro Glu
 1               5                  10                  15

Glu Val Tyr Val Ile Val Glu Ile Pro Arg Gly Ser Arg Val Lys Tyr
                20                  25                  30

Glu Ile Ala Lys Asp Phe Pro Gly Met Leu Val Asp Arg Val Leu Tyr
            35                  40                  45

Ser Ser Val Val Tyr Pro Val Asp Tyr Gly Leu Ile Pro Arg Thr Leu
        50                  55                  60
```

```
Tyr Tyr Asp Gly Asp Pro Met Asp Val Met Val Leu Ile Ser Gln Pro
 65                  70                  75                  80

Thr Phe Pro Gly Ala Ile Met Lys Val Arg Pro Ile Gly Met Met Lys
                 85                  90                  95

Met Val Asp Gln Gly Glu Thr Asp Asn Lys Ile Leu Ala Val Phe Asp
            100                 105                 110

Lys Asp Pro Asn Val Ser Tyr Ile Lys Asp Leu Lys Asp Val Asn Ala
        115                 120                 125

His Leu Leu Asp Glu Ile Ala Asn Phe Phe Ser Thr Tyr Lys Ile Leu
    130                 135                 140

Glu Lys Lys Glu Thr Lys Val Leu Gly Trp Glu Gly Lys Glu Ala Ala
145                 150                 155                 160

Leu Lys Glu Ile Glu Val Ser Ile Lys Met Tyr Glu Glu Lys Tyr Gly
                165                 170                 175

Lys Lys Asn

<210> SEQ ID NO 11
<211> LENGTH: 89
<212> TYPE: DNA
<213> ORGANISM: Artificial Sequence
<220> FEATURE:
<223> OTHER INFORMATION: Description of Artificial Sequence: Modified
      polylinker sequence of pTTQ18NHK

<400> SEQUENCE: 11
atgcaccacc accaccacca tatgggcatg ctgaattcga gctcggtacc cggggatcct     60
ctagagtcga cctgcaggca tgcaagctt                                       89

<210> SEQ ID NO 12
<211> LENGTH: 5503
<212> TYPE: DNA
<213> ORGANISM: Artificial Sequence
<220> FEATURE:
<223> OTHER INFORMATION: Description of Artificial Sequence: pTTQ18NHK
      vector
<220> FEATURE:
```

<210> SEQ ID NO 10
<211> LENGTH: 686
<212> TYPE: DNA
<213> ORGANISM: Aeropyrum pernix

<400> SEQUENCE: 10

```
tgcatgcata tgacaggctg tctgaaaatt ggtcctggag atgaggctcc agatgttgtg     60
aatgtcgtta tagagatacc tatgaacagt tctgttaagt acgagttcga caaggaggcg    120
tgtattgtta aggttgatag gttcctttac accagcatgg tctacccctt caactacggg    180
ttcataccag gcactctaga ggaggacgga gatcctgttg acgttctagt tattagccgg    240
gagcccgttg ctcccggctc gcttatagag gctgtgcccg tggccgtgtt agacatggag    300
gacgaggagg gtccggacag caaggttgtt gccgtaccca aggccaagct ggacccccta    360
ttcgccagct ataaggacgt tggcgacata cctgatgccc tgaaatccaa gataaagcac    420
ttcttcgagc actataagga gctggagcct ggaaagtggg ttagagtgac tggatggagg    480
cctgctgccg atgcgaagga gattataagg agggctatag agaggtataa gggggcgtga    540
tgagggctta acggctcacg ttttctggga gagtgtcgca cctttgaggg cgatcaccct    600
cgccagcgtg cgtgtgcttt tgtctatgat tatggctaca gttcttctag ccgctttcac    660
cgcccccaca gtcaagctta cactta                                         686
```

<221> NAME/KEY: misc_feature
<222> LOCATION: (3279, 3525)
<223> OTHER INFORMATION: n is a or g or c or t

<400> SEQUENCE: 12

```
gaactggatc tcaacagcgg taagatcctt gagagttttc gccccgaaga acgttttcca      60
atgatgagca cttttaaagt tctgctatgt ggcgcggtat tatcccgtat tgacgccggg     120
caagagcaac tcggtcgccg catacactat tctcagaatg acttggttga gtactcacca     180
gtcacagaaa agcatcttac ggatggcatg acagtaagag aattatgcag tgctgccata     240
accatgagtg ataacactgc ggccaactta cttctgacaa cgatcggagg accgaaggag     300
ctaaccgctt ttttgcacaa catgggggat catgtaactc gccttgatcg ttgggaaccg     360
gagctgaatg aagccatacc aaacgacgag cgtgacacca cgatgcctgt agcaatggca     420
acaacgttgc gcaaactatt aactggcgaa ctacttactc tagcttcccg gcaacaatta     480
atagactgga tggaggcgga taagttgca ggaccactt tgcgctcggc ccttccggct     540
ggctggttta ttgctgataa atctggagcc ggtgagcgtg gtctcgcgg tatcattgca     600 gcactggggc cagatggtaa gccctcccgt atcgtagtta tctacacgac ggggagtcag     660
gcaactatgg atgaacgaaa tagacagatc gctgagatag gtgcctcact gattaagcat     720
tggtaactgt cagaccaagt ttactcatat atactttaga ttgatttaaa acttcatttt     780
taatttaaaa ggatctaggt gaagatcctt tttgataatc tcatgaccaa aatcccttaa     840
cgtgagtttt cgttccactg agcgtcagac cccgtagaaa agatcaaagg atcttcttga     900
gatccttttt ttctgcgcgt aatctgctgc ttgcaaacaa aaaaaccacc gctaccagcg     960
gtggtttgtt tgccggatca agagctacca actctttttc cgaaggtaac tggcttcagc    1020
agagcgcaga taccaaatac tgtccttcta gtgtagccgt agttaggcca ccacttcaag    1080
aactctgtag caccgcctac atacctcgct ctgctaatcc tgttaccagt ggctgctgcc    1140
agtggcgata agtcgtgtct taccgggttg gactcaagac gatagttacc ggataaggcg    1200
cagcggtcgg gctgaacggg gggttcgtgc acacagccca gcttggagcg aacgacctac    1260
accgaactga gatacctaca gcgtgagcat tgagaaagcg ccacgcttcc cgaagggaga    1320
aaggcggaca ggtatccggt aagcggcagg gtcggaacag gagagcgcac gagggagctt    1380
ccagggggaa acgcctggta tctttatagt cctgtcgggt ttcgccacct ctgacttgag    1440
cgtcgatttt tgtgatgctc gtcagggggg cggagcctat ggaaaaacgc cagcaacgcg    1500
gcctttttac ggttcctggc cttttgctgg ccttttgctc acatgttctt tcctgcgtta    1560
tcccctgatt ctgtggataa ccgtattacc gcctttgagt gagctgatac cgctcgccgc    1620
agccgaacga ccgagcgcag cgagtcagtg agcgaggaag cggaagagcg cccaatacgc    1680
aaaccgcctc tccccgcgcg ttggccgatt cattaatgca gaattaattc tcatgtttga    1740
cagcttatca tcgactgcac ggtgcaccaa tgcttctggc gtcaggcagc catcggaagc    1800
tgtggtatgg ctgtgcaggt cgtaaatcac tgcataattc gtgtcgctca aggcgcactc    1860
ccgttctgga taatgttttt tgcgccgaca tcataacggt tctggcaaat attctgaaat    1920
gagctgttga caattaatca tcggctcgta taatgtgtgg aattgtgagc ggataacaat    1980
ttcacacagg aaacacatat atgcaccacc accaccacca tatgggcatg ctgaattcga    2040
gctcggtacc cggggatcct ctagagtcga cctgcaggca tgcaagcttg cactggccg     2100 tcgttttaca acgtcgtgac tgggaaaacc ctggcgttac ccaacttaat cgccttgcag    2160
cacatccccc tttcgccagc tggcgtaata gcgaagaggc ccgcaccgat cgcccttccc    2220
```

```
aacagttgcg cagcctgaat ggcgaatggc gcctgatgcg gtattttctc cttacgcatc   2280
tgtgcggtat ttcacaccgc ataaattccc tgttttggcg gatgagagaa gattttcagc   2340
ctgatacaga ttaaatcaga acgcagaagc ggtctgataa acagaatttt gcctggcggc   2400
agtagcgcgg tggtcccacc tgaccccatg ccgaactcag aagtgaaacg ccgtagcgcc   2460
gatggtagtg tggggtctcc ccatgcgaga gtagggaact gccaggcatc aaataaaacg   2520
aaaggctcag tcgaaagact gggcctttcg ttttatctgt tgtttgtcgg tgaacgctct   2580
cctgagtagg acaaatccgc cgggagcgga tttgaacgtt gcgaagcaac ggcccggagg   2640
gtggcgggca ggacgcccgc cataaactgc caggcatcaa attaagcaga aggccatcct   2700
gacggatggc cttttgcgt ttctacaaac tcttcctgtc gtcatatcta caagccatcc   2760
ccccacagat acggtaaact agcctcgttt ttgcatcagg aaagcaggga atttatggtg   2820
cactctcagt acaatctgct ctgatgccgc atagttaagc cagccccgac acccgccaac   2880
acccgctgac gcgccctgac gggcttgtct gctcccggca tccgcttaca gacaagctgt   2940
gaccgtctcc gggagctgca tgtgtcagag gttttcaccg tcatcaccga aacgcgcgag   3000
acgaaagggc ctgattagaa aaactcatcg agcatcaaat gaaactgcaa tttattcata   3060
tcaggattat caataccata ttttgaaaa agccgtttct gtaatgaagg agaaaactca   3120
ccgaggcagt tccataggat ggcaagatcc tggtatcggt ctgcgattcc gactcgtcca   3180
acatcaatac aacctattaa ttttccctcg tcaaaaataa ggttatcaag tgagaaatca   3240
ccatgagtga cgactgaatc cggtgagaat ggcaaaagnt tatgcatttc tttccagact   3300
tgttcaacag gccagccatt acgctcgtca tcaaaatcac tcgcatcaac caaaccgtta   3360
ttcattcgtg attgcgcctg agcgagacga atacgcgat cgctgttaaa aggacaatta   3420
caaacaggaa tcgaatgcaa ccggcgcagg aacactgcca gcgcatcaac aatattttca   3480
cctgaatcag gatattcttc taatacctgg aatgctgttt tcccngggat cgcagtggtg   3540
agtaaccatg catcatcagg agtacggata aaatgcttga tggtcggaag aggcataaat   3600
tccgtcagcc agtttagtct gaccatctca tctgtaacat cattggcaac gctacctttg   3660
ccatgtttca gaaacaactc tggcgcatcg gcttcccat acaatcgata gattgtcgca   3720
cctgattgcc cgacattatc gcgagcccat ttatacccat ataaatcagc atccatgttg   3780
gaatttaatc gcggcctcga caagacgtt tcccgttgaa tatggctcat aacacccctt   3840
gtattactgt ttatgtaagc agacagtttt attgttcatg atgatatatt tttatcttgt   3900
gcaatgtaac atcagggcct cgtgatacgc ctatttttat aggttaatgt catgataata   3960
atggtttctt agacgtgagg ttctgtaccc gacaccatcg aatggtgcaa aacctttcgc   4020
ggtatggcat gatagcgccc ggaagagagt caattcaggg tggtgaatgt gaaaccagta   4080
acgttatacg atgtcgcaga gtatgccggt gtctcttatc agaccgtttc ccgcgtggtg   4140
aaccaggcca gccacgtttc tgcgaaaacg cgggaaaaag tggaagcggc gatggcggag   4200
ctgaattaca ttcccaaccg cgtggcacaa caactggcgg gcaaacagtc gttgctgatt   4260
ggcgttgcca cctccagtct ggccctgcac gcgccgtcgc aaattgtcgc ggcgattaaa   4320
tctcgcgccg atcaactggg tgccagcgtg gtggtgtcga tggtagaacg aagcggcgtc   4380
gaagcctgta aagcggcggt gcacaatctt ctcgcgcaac gcgtcagtgg gctgatcatt   4440
aactatccgc tggatgacca ggatgccatt gctgtggaag ctgcctgcac taatgttccg   4500
gcgttatttc ttgatgtctc tgaccagaca cccatcaaca gtattatttt ctcccatgaa   4560
```

-continued

```
gacggtacgc gactgggcgt ggagcatctg gtcgcattgg gtcaccagca aatcgcgctg    4620
ttagcgggcc cattaagttc tgtctcggcg cgtctgcgtc tggctggctg gcataaatat    4680
ctcactcgca atcaaattca gccgatagcg gaacgggaag gcgactggag tgccatgtcc    4740
ggttttcaac aaaccatgca aatgctgaat gagggcatcg ttcccactgc gatgctggtt    4800
gccaacgatc agatggcgct gggcgcaatg cgcgccatta ccgagtccgg gctgcgcgtt    4860
ggtgcggata tctcggtagt gggatacgac gataccgaag acagctcatg ttatatcccg    4920
ccgttaacca ccatcaaaca ggattttcgc ctgctgggc aaaccagcgt ggaccgcttg     4980
ctgcaactct ctcagggcca ggcggtgaag gcaatcagc tgttgcccgt ctcactggtg     5040
aaaagaaaaa ccaccctggc gcccaatacg caaaccgcct ctccccgcgc gttggccgat    5100
tcattaatgc agctggcacg acaggtttcc cgactgaaa gcgggcagtg agcgcaacgc     5160
aattaatgta agttagctca ctcattaggc accccaggct ttacacttta tgcttccgac    5220
ctgcaagaac ctcacgtcag gtggcacttt tcggggaaat gtgcgcggaa cccctatttg    5280
tttatttttc taaatacatt caaatatgta tccgctcatg agacaataac cctgataaat    5340
gcttcaataa tattgaaaaa ggaagagtat gagtattcaa catttccgtg tcgcccttat    5400
tccctttttt gcggcatttt gccttcctgt ttttgctcac ccagaaacgc tggtgaaagt    5460
aaaagatgct gaagatcagt tgggtgcacg agtgggttac atc                      5503
```

<210> SEQ ID NO 13
<211> LENGTH: 6105
<212> TYPE: DNA
<213> ORGANISM: Artificial Sequence
<220> FEATURE:
<223> OTHER INFORMATION: Description of Artificial Sequence: pTTQ18NHK
    vector including the PPase sequence
<220> FEATURE:
<221> NAME/KEY: misc_feature
<222> LOCATION: (3881, 4127)
<223> OTHER INFORMATION: n is a or g or c or t

<400> SEQUENCE: 13

```
gaactggatc tcaacagcgg taagatcctt gagagttttc gccccgaaga acgttttcca     60
atgatgagca cttttaaagt tctgctatgt ggcgcggtat tatcccgtat tgacgccggg    120
caagagcaac tcggtcgccg catacactat tctcagaatg acttggttga gtactcacca    180
gtcacagaaa agcatcttac ggatggcatg acagtaagag aattatgcag tgctgccata    240
accatgagtg ataacactgc ggccaactta cttctgacaa cgatcggagg accgaaggag    300
ctaaccgctt ttttgcacaa catgggggat catgtaactc gccttgatcg ttgggaaccg    360
gagctgaatg aagccatacc aaacgacgag cgtgacacca cgatgcctgt agcaatggca    420
acaacgttgc gcaaactatt aactggcgaa ctacttactc tagcttcccg gcaacaatta    480
atagactgga tggaggcgga taaagttgca ggaccacttc tgcgctcggc ccttccggct    540
ggctggttta ttgctgataa atctggagcc ggtgagcgtg ggtctcgcgg tatcattgca    600
gcactggggc cagatggtaa gccctcccgt atcgtagtta tctacacgac ggggagtcag    660
gcaactatgg atgaacgaaa tagacagatc gctgagatag gtgcctcact gattaagcat    720
tggtaactgt cagaccaagt ttactcatat atactttaga ttgatttaaa acttcatttt    780
taatttaaaa ggatctaggt gaagatcctt tttgataatc tcatgaccaa aatcccttaa    840
cgtgagtttt cgttccactg agcgtcagac cccgtagaaa agatcaaagg atcttcttga    900
gatccttttt ttctgcgcgt aatctgctgc ttgcaaacaa aaaaaccacc gctaccagcg    960
```

```
gtggtttgtt tgccggatca agagctacca actctttttc cgaaggtaac tggcttcagc   1020
agagcgcaga taccaaatac tgtccttcta gtgtagccgt agttaggcca ccacttcaag   1080
aactctgtag caccgcctac atacctcgct ctgctaatcc tgttaccagt ggctgctgcc   1140
agtggcgata agtcgtgtct taccggggttg gactcaagac gatagttacc ggataaggcg   1200
cagcggtcgg gctgaacggg gggttcgtgc acacagccca gcttggagcg aacgacctac   1260
accgaactga gatacctaca gcgtgagcat tgagaaagcg ccacgcttcc cgaagggaga   1320
aaggcggaca ggtatccggt aagcggcagg gtcggaacag gagagcgcac gagggagctt   1380
ccagggggaa acgcctggta tctttatagt cctgtcgggt ttcgccacct ctgacttgag   1440
cgtcgatttt tgtgatgctc gtcaggggg cggagcctat ggaaaaacgc cagcaacgcg   1500 gccttttttac ggttcctggc cttttgctgg ccttttgctc acatgttctt tcctgcgtta   1560
tcccctgatt ctgtggataa ccgtattacc gcctttgagt gagctgatac cgctcgccgc   1620
agccgaacga ccgagcgcag cgagtcagtg agcgaggaag cggaagagcg cccaatacgc   1680
aaaccgcctc tccccgcgcg ttggccgatt cattaatgca gaattaattc tcatgtttga   1740
cagcttatca tcgactgcac ggtgcaccaa tgcttctggc gtcaggcagc catcggaagc   1800
tgtggtatgg ctgtgcaggt cgtaaatcac tgcataattc gtgtcgctca aggcgcactc   1860
ccgttctgga taatgttttt tgcgccgaca tcataacggt tctggcaaat attctgaaat   1920
gagctgttga caattaatca tcggctcgta taatgtgtgg aattgtgagc ggataacaat   1980
ttcacacagg aaacacatat atgcaccacc accaccacca tatgacaggc tgtctgaaaa   2040
ttggtcctgg agatgaggct ccagatgttg tgaatgtcgt tatagagata cctatgaaca   2100
gttctgttaa gtacgagttc gacaaggagg cgtgtattgt taaggttgat aggttccttt   2160
acaccagcat ggtctacccc ttcaactacg ggttcatacc aggcactcta gaggaggacg   2220
gagatcctgt tgacgttcta gttattagcc gggagcccgt tgctcccggc tcgcttatag   2280
aggctgtgcc cgtggccgtg ttagacatgg aggacgagga gggtccggac agcaaggttg   2340
ttgccgtacc caaggccaag ctggacccccc tattcgccag ctataaggac gttggcgaca   2400
tacctgatgc cctgaaatcc aagataaagc acttcttcga gcactataag gagctggagc   2460
ctggaaagtg ggtttagagtg actggatgga ggcctgctgc cgatgcgaag gagattataa   2520
ggagggctat agagaggtat aagggggcgt gatgagggct taacggctca cgttttctgg   2580
gagagtgtcg cacctttgag ggcgatcacc ctcgccagcg tgcgtgtgct tttgtctatg   2640
attatggcta cagttcttct agccgctttc accgccccca cagtcaagct tggcactggc   2700
cgtcgtttta caacgtcgtg actgggaaaa ccctggcgtt acccaactta atcgccttgc   2760
agcacatccc cctttcgcca gctggcgtaa tagcgaagag gcccgcaccg atcgcccttc   2820
ccaacagttg cgcagcctga atggcgaatg gcgcctgatg cggtatttttc tccttacgca   2880 tctgtgcggt atttcacacc gcataaattc cctgttttgg cggatgagag aagattttca   2940
gcctgataca gattaaatca gaacgcagaa gcggtctgat aaaacagaat ttgcctggcg   3000
gcagtagcgc ggtggtccca cctgaccccca tgccgaactc agaagtgaaa cgccgtagcg   3060
ccgatggtag tgtggggtct ccccatgcga gagtagggaa ctgccaggca tcaaataaaa   3120
cgaaaggctc agtcgaaaga ctgggccttt cgttttatct gttgtttgtc ggtgaacgct   3180
ctcctgagta ggacaaatcc gccgggagcg atttgaacg ttgcgaagca acggcccgga   3240
gggtggcggg caggacgccc gccataaact gccaggcatc aaattaagca gaaggccatc   3300
ctgacggatg ccttttttgc gtttctacaa actcttcctg tcgtcatatc tacaagccat   3360
```

-continued

```
cccccccacag atacggtaaa ctagcctcgt ttttgcatca ggaaagcagg gaatttatgg      3420
tgcactctca gtacaatctg ctctgatgcc gcatagttaa gccagccccg acacccgcca      3480 acaccegctg acgcgccctg acgggcttgt ctgctcccgg catccgctta cagacaagct      3540
gtgaccgtct ccgggagctg catgtgtcag aggttttcac cgtcatcacc gaaacgcgcg      3600
agacgaaagg gcctgattag aaaaactcat cgagcatcaa atgaaactgc aatttattca      3660
tatcaggatt atcaatacca tattttttgaa aaagccgttt ctgtaatgaa ggagaaaact      3720
caccgaggca gttccatagg atggcaagat cctggtatcg gtctgcgatt ccgactcgtc      3780
caacatcaat acaacctatt aatttcccct cgtcaaaaat aaggttatca agtgagaaat      3840
caccatgagt gacgactgaa tccggtgaga atggcaaaag nttatgcatt tctttccaga      3900
cttgttcaac aggccagcca ttacgctcgt catcaaaatc actcgcatca accaaaccgt      3960
tattcattcg tgattgcgcc tgagcgagac gaaatacgcg atcgctgtta aaaggacaat      4020
tacaaacagg aatcgaatgc aaccggcgca ggaacactgc cagcgcatca acaatatttt      4080
cacctgaatc aggatattct tctaataccct ggaatgctgt tttcccnggg atcgcagtgg      4140
tgagtaacca tgcatcatca ggagtacgga taaaatgctt gatggtcgga agaggcataa      4200
attccgtcag ccagtttagt ctgaccatct catctgtaac atcattgca acgctacctt      4260 tgccatgttt cagaaacaac tctggcgcat cgggcttccc atacaatcga tagattgtcg      4320
cacctgattg cccgacatta tcgcgagccc atttataccc atataaatca gcatccatgt      4380 tggaattttaa tcgcggcctc gagcaagacg tttcccgttg aatatggctc ataacacccc      4440
ttgtattact gtttatgtaa gcagacagtt ttattgttca tgatgatata ttttatcttt      4500
gtgcaatgta acatcaggc ctcgtgatac gcctattttt ataggttaat gtcatgataa      4560
taatggtttc ttagacgtga ggttctgtac ccgacaccat cgaatggtgc aaaacctttc      4620
gcggtatggc atgatagcgc ccggaagaga gtcaattcag ggtggtgaat gtgaaaccag      4680
taacgttata cgatgtcgca gagtatgccg gtgtctctta tcagaccgtt tcccgcgtgg      4740
tgaaccaggc cagccacgtt tctgcgaaaa cgcgggaaaa agtggaagcg gcgatggcgg      4800
agctgaatta cattcccaac cgcgtggcac aacaactggc gggcaaacag tcgttgctga      4860
ttggcgttgc cacctccagt ctggccctgc acgcgccgtc gcaaattgtc gcggcgatta      4920
aatctcgcgc cgatcaactg ggtgccagcg tggtggtgtc gatggtagaa cgaagcggcg      4980
tcgaagcctg taaagcggcg gtgcacaatc ttctcgcgca acgcgtcagt gggctgatca      5040
ttaactatcc gctggatgac caggatgcca ttgctgtgga agctgcctgc actaatgttc      5100
cggcgttatt tcttgatgtc tctgaccaga cacccatcaa cagtattatt ttctcccatg      5160
aagacggtac gcgactgggc gtggagcatc tggtcgcatt gggtcaccag caaatcgcgc      5220
tgttagcggg cccattaagt tctgtctcgg cgcgtctgcg tctggctggc tggcataaat      5280
atctcactcg caatcaaatt cagccgatag cggaacggga aggcgactgg agtgccatgt      5340
ccggttttca acaaaccatg caaatgctga atgagggcat cgttcccact gcgatgctgg      5400
ttgccaacga tcagatggcg ctgggcgcaa tgcgcgccat taccgagtcc gggctgcgcg      5460
ttggtgcgga tatctcggta gtgggatacg acgataccga agacagctca tgttatatcc      5520
cgccgttaac caccatcaaa caggattttc gcctgctggg gcaaaccagc gtggaccgct      5580
tgctgcaact ctctcagggc caggcggtga agggcaatca gctgttgccc gtctcactgg      5640
tgaaaagaaa aaccaccctg gcgcccaata cgcaaaccgc ctctccccgc gcgttggccg      5700
```

```
attcattaat gcagctggca cgacaggttt cccgactgga aagcgggcag tgagcgcaac    5760
gcaattaatg taagttagct cactcattag gcaccccagg ctttacactt tatgcttccg    5820
acctgcaaga acctcacgtc aggtggcact tttcggggaa atgtgcgcgg aaccnctatt    5880
```

```
attcattaat gcagctggca cgacaggttt cccgactgga aagcgggcag tgagcgcaac    5760
gcaattaatg taagttagct cactcattag gcaccccagg ctttacactt tatgcttccg    5820
acctgcaaga acctcacgtc aggtggcact tttcggggaa atgtgcgcgg aaccnctatt    5880
tgtttatttt tctaaataca ttcaaatatg tatccgctca tgagacaata accctgataa    5940
atgcttcaat aatattgaaa aaggaagagt atgagtattc aacatttccg tgtcgccctt    6000
attccctttt ttgcggcatt ttgccttcct gttttttgctc acccagaaac gctggtgaaa    6060
gtaaaagatg ctgaagatca gttgggtgca cgagtgggtt acatc                    6105
```

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 14
gatgagttcg tgtccgtaca actgg                                            25

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 15
ggttatcgaa atcagccaca gcgcc                                            25

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 16
gcaacgcccc tcactataaa                                                  20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 17
gcaccccgcc cttgaagtcc                                                  20

<210> SEQ ID NO 18
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 18
tgcatgcata tgacaggctg tctgaaaatt g                                     31

<210> SEQ ID NO 19
<211> LENGTH: 33
<212> TYPE: DNA
<213> ORGANISM: Artificial Sequence
```

```
<220> FEATURE:
<223> OTHER INFORMATION: Description of Artificial Sequence: Primer

<400> SEQUENCE: 19
taagtgtaag cttgactgtg ggggcggtga aag                              33

<210> SEQ ID NO 20
<211> LENGTH:
<212> TYPE:
<213> ORGANISM:

<400> SEQUENCE: 20

000

<210> SEQ ID NO 21
<211> LENGTH:
<212> TYPE:
<213> ORGANISM:

<400> SEQUENCE: 21

000

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 22
gactcgtcat actcctgctt gct                                        23

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 23
cattgccgac aggatgcaga a                                          21

<210> SEQ ID NO 24
<211> LENGTH: 27
<212> TYPE: DNA
<213> ORGANISM: Artificial Sequence
<220> FEATURE:
<223> OTHER INFORMATION: Description of Artificial Sequence: Probe

<400> SEQUENCE: 24
atccacatct gctggaaggt ggacagt                                    27

<210> SEQ ID NO 25
<211> LENGTH: 176
<212> TYPE: PRT
<213> ORGANISM: Aeropyrum pernix

<400> SEQUENCE: 25
```

Met Thr Gly Cys Leu Lys Ile Gly Pro Gly Asp Glu Ala Pro Asp Val
 1               5                  10                  15

Val Asn Val Val Ile Glu Ile Pro Met Asn Ser Ser Val Lys Tyr Glu
                20                  25                  30

Phe Asp Lys Glu Ala Cys Ile Val Lys Val Asp Arg Phe Leu Tyr Thr
            35                  40                  45

-continued

```
Ser Met Val Tyr Pro Phe Asn Tyr Gly Phe Ile Pro Gly Thr Leu Glu
     50                  55                  60

Glu Asp Gly Asp Pro Val Asp Val Leu Val Ile Ser Arg Glu Pro Val
 65                  70                  75                  80

Ala Pro Gly Ser Leu Ile Glu Ala Val Pro Val Ala Val Leu Asp Met
                 85                  90                  95

Glu Asp Glu Glu Gly Pro Asp Ser Lys Val Val Ala Val Pro Lys Ala
            100                 105                 110

Lys Leu Asp Pro Leu Phe Ala Ser Tyr Lys Asp Val Gly Asp Ile Pro
            115                 120                 125

Asp Ala Leu Lys Ser Lys Ile Lys His Phe Phe Glu His Tyr Lys Glu
        130                 135                 140

Leu Glu Pro Gly Lys Trp Val Arg Val Thr Gly Trp Arg Pro Ala Ala
145                 150                 155                 160

Asp Ala Lys Glu Ile Ile Arg Arg Ala Ile Glu Arg Tyr Lys Gly Ala
                165                 170                 175
```

<210> SEQ ID NO 26
<211> LENGTH: 531
<212> TYPE: DNA
<213> ORGANISM: Aeropyrum pernix

<400> SEQUENCE: 26

```
atgacaggct gtctgaaaat tggtcctgga gatgaggctc cagatgttgt gaatgtcgtt      60
atagagatac ctatgaacag ttctgttaag tacgagttcg acaaggaggc gtgtattgtt     120
aaggttgata ggttccttta caccagcatg gtctacccct tcaactacgg gttcatacca     180
ggcactctag aggaggacgg agatcctgtt gacgttctag ttattagccg ggagcccgtt     240
gctcccggct cgcttataga ggctgtgccc gtggccgtgt tagacatgga ggacgaggag     300
ggtccggaca gcaaggttgt tgccgtaccc aaggccaagc tggacccct attcgccagc      360 tataaggacg ttggcgacat acctgatgcc ctgaaatcca agataaagca cttcttcgag     420
cactataagg agctggagcc tggaaagtgg gttagagtga ctggatggag gcctgctgcc     480
gatgcgaagg agattataag gagggctata gagaggtata aggggcgtg a               531
```